(12) United States Patent
Bahlmann et al.

(10) Patent No.: US 7,745,387 B2
(45) Date of Patent: Jun. 29, 2010

(54) USE OF ERYTHROPOIETIN

(75) Inventors: Ferdinand Hermann Bahlmann, Hannover (DE); Hermann Haller, Hannover (DE)

(73) Assignee: Epoplus GmbH & Co. KG (DE)

( * ) Notice: Subject to any disclaimer, the term of this patent is extended or adjusted under 35 U.S.C. 154(b) by 332 days.

(21) Appl. No.: 10/522,426

(22) PCT Filed: Jul. 25, 2003

(86) PCT No.: PCT/EP03/08229

§ 371 (c)(1),
(2), (4) Date: Mar. 25, 2005

(87) PCT Pub. No.: WO2004/012759

PCT Pub. Date: Feb. 12, 2004

(65) Prior Publication Data

US 2005/0272634 A1    Dec. 8, 2005

(30) Foreign Application Priority Data

Jul. 26, 2002   (DE) ................................ 102 34 192

(51) Int. Cl.
*A61K 38/00* (2006.01)
(52) U.S. Cl. ........................................................ 514/2
(58) Field of Classification Search ........................ None
See application file for complete search history.

(56) References Cited

U.S. PATENT DOCUMENTS

| | | | | |
|---|---|---|---|---|
| 4,992,419 | A | 2/1991 | Woog et al. | 514/8 |
| 5,198,417 | A | 3/1993 | Donahue et al. | 514/2 |
| 5,837,675 | A | 11/1998 | Brox | 514/8 |
| 5,980,887 | A | 11/1999 | Isner et al. | 424/93.7 |
| 6,274,158 | B1 * | 8/2001 | Zaharia | 424/423 |
| 6,284,260 | B1 | 9/2001 | Czeizler | 424/423 |
| 6,748,154 | B2 * | 6/2004 | O'Leary et al. | 385/135 |
| 6,784,154 | B2 * | 8/2004 | Westenfelder | 514/2 |
| 7,232,797 | B2 * | 6/2007 | Farrell et al. | 514/2 |
| 2002/0045255 | A1 | 4/2002 | Powell | 435/325 |

(Continued)

FOREIGN PATENT DOCUMENTS

DE    198 57 609 A1   6/2000

(Continued)

OTHER PUBLICATIONS

Fatouros MS et al "Influence of growth factors erythropoietin and granulocyte macrophage colony stimulating factor on mechanical strength and healing of colonic anastomoses in rats," Eur J Surg. Oct. 1999;165(10):986-92.*

(Continued)

*Primary Examiner*—Cecilia Tsang
*Assistant Examiner*—Thomas S Heard
(74) *Attorney, Agent, or Firm*—Ostrolenk Faber LLP

(57) ABSTRACT

The present invention relates to the use of erythropoietin for stimulating the physiological mobilization, proliferation and differentiation of endothelial progenitor cells, for stimulating vasculogenesis, for the therapy of diseases associated with a dysfunction of endothelial progenitor cells and for producing pharmaceutical compositions for the treatment of such diseases, and pharmaceutical compositions which comprise erythropoietin and other suitable active ingredients for stimulating endothelial progenitor cells.

7 Claims, 15 Drawing Sheets

U.S. PATENT DOCUMENTS

| | | | |
|---|---|---|---|
| 2002/0065214 A1 | 5/2002 | Iaina et al. | 514/2 |
| 2002/0137145 A1 | 9/2002 | Powell | 435/69.4 |
| 2003/0130197 A1* | 7/2003 | Smith-Swintosky et al. | 514/15 |

FOREIGN PATENT DOCUMENTS

| | | |
|---|---|---|
| EP | 0 456 153 B1 | 11/1991 |
| EP | 0613683 A1 * | 2/1994 |
| EP | 0 613 683 B1 | 9/1994 |
| WO | WO 87/03204 | 6/1987 |
| WO | WO 89/07944 | 9/1989 |
| WO | WO 89/07944 A | 9/1989 |
| WO | WO 92/15323 A | 9/1992 |
| WO | WO 96/14081 | 5/1996 |
| WO | WO 98/10650 | 3/1998 |
| WO | WO 98/10650 A | 3/1998 |
| WO | WO 00/35475 | 6/2000 |
| WO | WO 00/61164 | 10/2000 |
| WO | WO 00/61164 A | 10/2000 |
| WO | WO 01/82952 | 11/2001 |
| WO | WO 01/82953 | 11/2001 |
| WO | WO 02/14356 A2 | 2/2002 |
| WO | WO 02/053580 | 7/2002 |
| WO | WO 02/085940 A | 10/2002 |
| WO | WO 03/037273 | 5/2003 |
| WO | WO 03/037273 A2 | 5/2003 |
| WO | WO 03/057242 A1 | 7/2003 |
| WO | WO 2004/012759 A3 | 2/2004 |

OTHER PUBLICATIONS

Krussel JS, et al, "Vascular endothelial growth factor (VEGF) mRNA splice variants are differentially expressed in human blastocysts," Mol Hum Reprod. Jan. 2001;7(1):57-63.*

Janquet, Kai, et al., Brief Communication, Erythropoietin and VEGF Exhibit Equal giogenic Potential, Jun. 25, 2002, pp. 326-333 (from Applicant's IDS).*

Llevadot, Joan, et al., HMG-CoA Reductase Inhibitor Mobilizes Bone Marrow-Derived Engothelial Progenitor Cells, Apr. 26, 2001, pp. 399-405.

Jaquet, Kai, et al., Brief Communication Erythropoietin and VEGF Exhibit Equal Angiogenic Potential, Jun. 25, 2002, pp. 326-333.

Asahara, Takayuki, et al., VEGF Contributes to Postnatal Neovascularization By Mobilizing. Bone Marrow-Derived Endothelial Progenitor Cells, The EMBO Journal, vol. 18, No. 14; pp. 3964-3972, 1999.

Ribatti, D. "A potential role of erythropoietin in angiogenesis associated with myelodysplastic syndromes" *Leukemia*, 16(9):1890 (2002).

Catalano C., et al., "Erythropoietin is Beneficial in Mitomycin-Induced Hemolytic-Uremic Syndrome", *Nephron*, 91:324-326 (2002).

Quaschning T., et al., "Erythropoietin-induced excessive erythrocytosis activates the tissue endothelin system in mice." *The FASEB Journal*, 17(2):259-261 (2002).

Ribatti, D., et al., "Erythropoietin as an angionic factor in gastric carcinoma", *Histopathology*, 42(3):246-250 (2003).

Chong, Z. Z., et al., "Erythropoietin Is a Novel Vascular Protectant Through Activation of Akt1 and Mitochondrial Modulation of Cysteine Proteases" *Circulation*, 106(23):2973-2979 (2002).

Sanz, C., et al., "Nuclear Factor k B is activated in myelodysplastic bone marrow cells" *Haematologica*.

Z. Tongfeng, "Protective effect of L-arginine on acute renal failure", *J. Nephrol Daily Translplant*, 8(6):550-551 (1999).

Z. Yun, "Protective Effect of Simvastatin for Renal Function in Diabetic Nephropathies", *Chin. J. New Drugs Clin. Rem.*, 19(2):105-107 (2000).

International Search Report dated Apr. 20, 2004.

Zhao Zhong Chong, et al., "Angiogenesis and Plasticity: Role of Erythropoietin in Vascular Systems", *Journal of Hematotherapy & Stem Cell Research*, 11:863-871 (2002).

Dunst J., et al., Anemia and Elevated Systemic Levels of Vascular Endothelial Growth Factor (VEGF), *Strahlenther and Onkologie*, 8:436-441 (2002).

Kling, P.J., "Roles of erythropoietin in human milk", *Acta Pædiatr Suppl*, 438:31-35 (2002).

Borawski, J., et al., "Effects of Recombinant Erythropoietin Therapy on Circulating Endothelial Markers in Hemodialysis Patients", *Clin Appl Thrombosis/Hemostasis*, 8(1):77-84 (2002).

Gunga, H., et al., "Austrian Moderate Altitude Study (AMAS 2000)—fluid shifts, erythropoiesis, and angiogenesis in patients with metabolic syndrome at moderate altitude (≅1700 m)", *Eur J Appl Physiol*, 88:497-505 (2003).

Jaquet K., et al., "Erythropoietin and VEGF Exhibit Equal Angiogenic Potential", *Microvascular Research*, 64:326-333 (2002).

Yasuda, Y., et al., "Erythropoietin is involved in growth and angiogenesis in malignant tumours of female reproductive organs", *Carcinogenesis*, 23(11):1797-1805 (2002).

Suzuki, N., et al., "Erythroid-specific expression of the erythropoietin receptor rescued its null mutant mice from lethality", *Blood*, 100(7):2279-2288.

Buemi, M., et al., "Recombinant Human Erythropoietin Influences Revascularization and Healing in a Rat Model of Random Ischaemic Flaps", *Acta Derma Venereol*, 82:411-417 (2002).

Kapiteijn, K., et al., "Steroids and Cytokines in Endometrial Angiogenesis", *Anticancer Research*, 21:4231-4242 (2001).

Yasuda, Y., et al., "Expression of erythropoietin in human female reproductive organs", *Ital J Anat Embryol.*, 106(2 Suppl 2):215-222 (2001).

Wagner, P., et al., "Muscle angiogenic growth factor gene responses to exercise in chronic renal failure", *Am J Physiol Regulatory Integrative Physiol*, 281:R-539-R-546 (2001).

Noguchi, K. et al., "Effect of 1-week treatment with erythropoietin on the vascular endothelial function in anaesthetized rabbits", *British Journal of Pharmacology*, 133:395-405 (2001).

Raksuan K., et al., "Cardiac function, microvascular structure, and capillary hematocrit in hearts of polycythemic rats", *Am J Physiol Heart Circ Physiol*, 281:H2425-H2431 (2001).

Sasaki, R., et al., "Pleiotropic Functions and Tissue-Specific Expression of Erythropoietin", *News Physiol. Sci.*, 16:110-113 (2001).

Eckardt, K., "Anaemia in end-stage renal disease: pathophysiological considerations" *Nephrol Dial Transplant*, 16(Suppl 7):2-8 (2001).

Wiessner, C., et al., "Increased Cerebral Infarct Volumes in Polyglobulic Mice Overexpressing Erythropoietin", *Journal of Cerebral Blood Flow and Metabolism*, 21:857-864 (2001).

Kobayashi, T, et al., "Effects of Recombinant Human Erythropoietin Therapy on Blood Coagulation and Fibrinolysis System", *Ann Thorac Cardiovasc Surg*, 7(5):273-277 (2001).

Locatelli, F., et al., "Cardiovascular disease determinants in chronic renal failure: clinical approach and treatment" *Nephrol Dial Transplant*, 16:459-468 (2001).

Matsuzaki, S., et al., "Erythropoietin concentrations are elevated in the peritoneal fluid of women with endometriosis", *Human Reproduction*, 16(5):945-948 (2001).

Prchal, J.T., et al., "Lessons to better understanding of hypoxia sensing. Acquired and congenital mutations resulting in polycythemia", *Adv Exp Med Biol.*, 502:189-205 (2001).

Vaziri, N. D., "Cardiovascular effects of erythropoietin and anemia correction", *Curr Opin Nephrol Hypertens*, 10(5):633-637 (2001).

Pelletier, L., et al., "An In Vitro Model for the Study of Human Bone Marrow Angiogenesis: Role of Hematopoietic Cytokines", *Laboratory Investigation*, 80(4):501-511 (2000).

Metivier, F., et al., "Pathophysiology of anaemia: focus on the heart and blood vessels", *Nephrol Dial Transplant*, 15(Suppl 3):14-18 (2000).

Hsu, H., et al., "Hematopoietic stem cells express Tie-2 receptor in the murine fetal liver", *Blood*, 96(12):3757-3762 (2000).

Siren, A., et al., "Erythropoietin and erythropoietin receptor in human ischemic/hypoxic brain", *Acta Neuropathol*, 101:271-271 (2000).

Marti, H.H., et al., "Neuroprotection and Angiogenesis: Dual Role of Erythropoietin in Brain Ischemia", *News Physiol. Sci.*, 15:225-229 (2000).

Chikuma, M., et al., "Tissue-specific regulation of erythropoietin production in the murine kidney, brain, and uterus", *Am J Physiol Endocrinol Metab*, 279:E1242-E1248 (2000).

Banerjee, D., et al., "Exposure of endothelial cells to recombinant human erythropoietin induces nitric oxide synthase activity", *Kidney International*, 57:1895-1904 (2000).

Dicato, M., et al., "Clinical benefit from erythropoietin", *Curr Opin Oncol.*, 12(4):297-302 (2000).

Masuda, S., et al., "The oviduct produces erythropoietin in an estrogen- and oxygen-dependent manner", *Am J Physiol Endocrinol Metab*, 278:E1038-E1044 (2000).

Fatouros, M.S., et al., "Influence of Growth Factors Erythropoietin and Granulocyte Macrophage Colony Stimulating Factor on Mechanical Strength and Healing of Colonic Anastomoses in Rats", *Eur J Surg*, 165:986-992 (1999).

Fatouros, M., et al., "Alterations in body weight, breaking strength, and wound healing in Wistar rats treated pre- and postoperatively with erythropoietin or granulocyte macrophage-colony stimulating factor: Evidence of a previously unknown anabolic effect of erythropoietin", *J Lab Clin Med.*, 133(3):253-259 (1999).

Bernaudin, M., et al., "A Potential Role for Erythropoietin in Focal Permanent Cerebral Ischemia in Mice", *Journal of Cerebral Blood Flow & Metabolism*, 19:643-651 (1999).

Carlini, R.G., et al., "Effect of recombinant human erythropoietin on endothelial cell apoptosis", *Kidney International*, 55:546-553 (1999).

Ribatti, D., et al., "Human Erythropoietin Induces a Pro-Angiogenic Phenotype in Cultured Endothelial Cells and Stimulates Neovascularization In Vivo", *Blood*, 93(8):2627-2636 (1999).

Aguilera A., et al., "Effects of Recombinant Human Erythropoietin on Functional and Injury Endothelial Markers in Peritoneal Dialysis Patients", *Perit Dial Int.*, 19(Suppl 2):161-166 (1999).

Alvarez Arroyo, M.V., et al., "Role of vascular endothelial growth factor in the response to vessel injury", *Kidney International*, 54(68):7-9 (1998).

Graven, K.K., et al., "Endothelial cell hypoxic stress proteins", *J Lab Clin Med.*, 132(6):456-463 (1998).

Shih, S., et al., "Hypoxia-mediated regulation of gene expression in mammalian cells", *Int. J. Exp. Path.*, 79:247-257 (1998).

Yasuda, Y., et al., "Estrogen-dependent Production of Erythropoietin in Uterus and Its Implication in Unterine Angiogenesis", *The Journal of Biological Chemistry*, 273(39):25381-25387 (1998).

Wang, X.Q., et al., "Erythropoietin Depresses Nitric Oxide Synthase Expression by Human Endothelial Cells", *Hypertension*, 33(3):894-899 (1999).

Wenger, R.H., et al., "Oxygen(es) and the Hypoxia-Inducible Factor-1", *Biol. Chem*, 378:609-616 (1997).

Kremer, C., et al., "Up-Regulation of flk-1/Vascular Endothelial Growth Factor Receptor 2 by Its Ligand in a Cerebral Slice Culture System", *Cancer Research*, 57:3852-3859 (1997).

Sigounas, G., et al., "Synergism of Hemopoietic Growth Factors on Endothelial Cell Proliferation", *Angiology, the Journal of Vascular Diseases*, 48(2):141-147 (1997).

Tan, C.C, "Erythropoietin dysregulation in renal failure and research on IgA nephropathy" *Clinical Science Regional Focus Series*, 91(3):258-260 (1996).

Schmedtje, J.F., et al., "Evidence of Hypoxia-Inducible Factor-1 in Vascular Endothelial and Smooth Muscle Cells", *Biochemical and Biophysical Research Communications*, 220:687-691 (1996).

Yamaji, R., et al., "Brain capillary endothelial cells express two forms of erythropoietin receptor mRNA", *Eur. J. Biochem*, 239:494-500 (1996).

Bode-Böger, S.M., "Recombinant human erythropoietin enhances vasoconstrictor tone via endothelin-1 and constrictor prostanoids", *Kidney International*, 50(4):1255-1261 (1996).

Haller, H., et al., "Signal transduction of erythropoietin in endothelial cells", *Kidney International*, 50:481-488 (1996).

Kuriyama, S., et al., "Evidence for Amelioration of Endothelial Cell Dysfunction by Erythropoietin Therapy in Predialysis Patients", *American Journal of Hypertension*, 9(5):426-431 (1996).

Vittet, D., et al., "Embryonic Stem Cells Differentiate In Vitro to Endothelial Cells Through Successive Maturation Steps", *Blood*, 88(9):3424-3431 (1996).

Taylor, J.E., et al., "Peripheral microcirculatory blood flow in haemodialysis patients treated with erythropoietin", *International Angiology*, 15(1):33-38 (1996).

Bauer, C., "The oxygen sensor that controls EPO production: facts and fancies", *J Perinat Med.*, 23(1-2):7-12 (1995).

Carlini, R.G., et al., "Recombinant human erythropoietin stimulates angiogenisis in vitro", *Kidney International*, 47:740-745 (1995).

Nagai, T., et al., "Effects of rHuEpo on cellular proliferation and endothelin-1 production in cultured endothelial cells", *Nephrol Dial Transplant*, 10:1814-1819 (1995).

Niita, K., et al., "Endothelin-1 mediates erythropoietin-stimulated glomerular endothelial cell-dependent proliferation of messengial cells", *European Journal of Pharmacology*, 293:491-494 (1995).

Takahashi, S., et al., "Recombinant human erythropoietin has no direct or strong vasoconstrictor effects in vivo and in vitro", *Nephrol Dial Transplant*, 10:815-820 (1995).

Buemi, M., et al., "Recombinant Human Erythropoietin Inhibits the Cutanseous Vasodilatation Induced by Acetylcholine", *Int J. Microcirc*, 15:283-286 (1995).

Roche, R.J., "Does human recombinant erythropoietin improve wound healing?" *J Am Geriatr Soc.*, 43(1):81 (1995).

Bikfalvi, A., et al., "Angiogenic Factors are Hematopoietic Growth Factors and Vice Versa", *Leukemia*, 8(3):523-529 (1994).

Anagnostou, A., et al., "Erythropoietin receptor mRNA expression in human Endothelial cells", *Proc. Natl. Acad. Sci. USA*, 91:3974-3978 (1994).

Carlini, R.G., et al., "Recombinant human erythropoietin (rHuEPO) increases endothelin-1 release by endothelial cells", 43:1010-1014 (1993).

Muntzel, M., et al., "Effect of Erythropoietin on Hematocrit and Blood Pressure in Normotensive and Hypertensive Rats", *J. Am. Soc. Nephrol.*, 3:182-187 (1992).

Heidenreich, S., et al. "Direct vasopressor effect of recombinant human erythropoietin on renal resistance vessels", *Kidney International*, 39:259-265 (1991).

Yanai, N., et al., "Endothelial Cells Create a Hematopoietic Inductive Microenvironment Preferential to Erythropoiesis in the Mouse Spleen", *Cell Structure and Function*, 16:87-93 (1991).

Anagnostou, A., et al., "Erythropoietin has a mitogenic and positive chemoactic effect on endothelial cells", *Proc. Natl. Acad. Sci. USA*, 87:5978-5982 (1990).

Dainiak, N., et al., "Acetylated Lipoproteins Impair Erythroid Growth Factor Release from Endothelial Cells", *J. Clin. Invest.*, 81:834-843 (1988).

Naughton, G.K., et al., "Erythropoietin Production by Macrophages in the Regenerating Liver", *Journal of Surgical Oncology*, 30:184-197 (1985).

Ascensao, J.L., et al., "Role of Endothelial Cells in Human Hematopoiesis: Modulation of Mixed Colony Growth in Vitro", *Blood*, 63(3):553-558 (1984).

Buemi, M., et al., "Recombinant Erythropoietin Prevents the Progression of Atherosclerosis in Watanable Rabbits With Hereditary Hypocholesterolemia", *Nephrology Dialysis Transplantation*, 12(9):A190 (1997).

Buemi, M., et al., "Recombinant human erythropoietin (rHuEPO): More than just the correction of uremic anemia", *J. Nephrol.*, 15:97-103 (2002).

Masuda, S., et al., "Erythropoietin, neurotrophic, and angiogenic functions of erythropoietin and regulation of erythropoietin production", *International Journal of Hematology*, 70(1):1-6 (1999).

Krause, K., et al., "Recombinant human erythropoietin and VEGF have equal angiogenic potency: Investigation in a novel in vitro assay of human vascular tissues", *European Heart Journal*, 22:154 (2001).

Maschio, G., "Erythropoietin and systemic hypertension", *Nephrol. Dial. Transplant*, 10(Suppl. 2):74-79 (1995).

Kashiwagi, M., et al., "Hypertension in a pregnancy with renal anemia after reconbinant human erythropoietin (rhEPO) therapy", *Archives of Gynecology and Obstetrics*, 267(1):54-56 (2002).

Conrad Kirk, P., et al., "Placental cytokines and the pathogenesis of preeclampsia", *American Journal of Reproductive Immunology*, 37(3):240-249 (1997).

Cases, A., "Recombinant human erythropoietin treatment in chronic renal failure: Effects on hemostasis and vasculature", *Drugs of Today 2000*, 36(8):541-556 (2000).

Braga, J., et al., "Maternal and perinatal implications of the use of human recombinant erythropoietin", *Acta Obstetricta Et Gynecologica*, 75(5):449-3 (1996).

Arcasoy Murat, O., et al., "Erythropoietin (EPO) stimulates angiogenisis in vivo and promotes would healing", *Blood*, 98(11):822a-823a (2001).

Alvarez Arroyo Maria Victoria, et al., "Role of vascular endothelial growth factor on erythropoietin-related endothelial cell proliferation", *Journal of the American Society of Nephrology*, 9(11):1998-2004 (1998).

Singapore Search Report and Written Opinion mailed Nov. 30, 2009 in corresponding Singapore Application No. 200700389-0 (English language).

Japanese Office Action mailed Mar. 9 2010 in corresponding Japanese Patent Application No. 2004-525322 (English language).

Montini, G., et al. "Pharmacokinetics and Hematologic Response to Subcutaneous Administration of Recombinant Human Erythropoietin In Children Undergoing Long-Term Peritoneal Dialysis: A Multicenter Study," J. Pediatr., 1993, vol. 122, No. 2, pp. 297-302.

Matuszkiewicz-Rowinska, J. et al. "Effect of Low-Dose Recombinant Humane Erythropoietin Therapy On The Quality Of Life In Patients With Anemia In The Course of End-Stage Renal Failure Treated With Dialysis," Pol Arch Med Wewn, 1996, vol. 96, No. 2, pp. 143-52 (Abstract), Medline [online], Accession No. 1997240098, PubMed ID 9122002.

Korean Office Action dated Mar. 22, 2010 in corresponding Korean Patent Application No. 10-2005-7001341 (English language).

N. D. Vaziri, et al. "Erythropoietin Enhances Recovery From Cisplatin-Induced Acute Renal Failure," American Journal of Psysiology, vol. 266, F360-F366 (1994).

\* cited by examiner

USE OF ERYTHROPOIETIN

The present invention relates to the use of erythropoietin for stimulating the physiological mobilization, proliferation and differentiation of endothelial progenitor cells, for stimulating vasculogenesis, for the therapy of diseases associated with a dysfunction of endothelial progenitor cells and for producing pharmaceutical compositions for the treatment of such diseases, and pharmaceutical compositions which comprise erythropoietin and other suitable active ingredients for stimulating endothelial progenitor cells.

The vascular endothelium is a layer of cells which lines blood vessels. The endothelium separates the blood from other vessel layers, and the endothelium does not just represent a passive barrier but is actively involved in regulating vessel tone. Reference is also accordingly made to endothelium-dependent vasodilatation. As a result of its position, the endothelium is permanently exposed to hemodynamic stress and metabolic stress. Pathogenic conditions, for example elevated blood pressure, elevated LDL levels, impaired kidney function or elevated blood glucose, are therefore frequently associated with functional endothelial defects which may then be followed by morphologically detectable lesions such as the formation of atherosclerotic plaques. A very early sign of an altered or diminished endothelial function, or endothelial dysfunction, is a reduction in the endothelium-dependent vasodilatation.

In coronary heart disease (CHD), but also when risk factors are present without CHD, for example hypertension, hyperlipoproteinemia or diabetes, the defects in endothelial function are manifested by a reduced production of NO (=EDRF) and increased endothelin production. High plasma levels of endothelin lead to abnormal adhesion of cells, inflammations, vascular proliferation and severe vessel constrictions. Disturbances of endothelial function are additionally characterized by increased production of adhesion molecules such as ICAM-1 and VCAM-1, causing platelets and monocytes to adhere to an increased extent to endothelium. The result of this is an increase in vessel tone. Thus, an imbalance develops in various systems, favoring vasoconstriction, adhesion, aggregation, coagulation, atherosclerosis and atherothrombosis. Even mental stress leads to a measurable endothelial dysfunction which may persist for up to 4 hours.

Endothelial cells are involved in the formation of new blood vessels. The formation of blood vessels is important in a large number of processes such as, for example, embryogenesis, the female reproductive cycle, wound healing, tumor growth and the neovascularization of ischemic areas. Originally, postnatal formation of blood vessels, that is the formation of blood vessels after birth, was mainly attributed to angiogenic processes. Angiogenesis means the formation of new blood vessels through capillaries sprouting from a pre-existing vascular system. During angiogenesis, firstly the basement membrane surrounding the blood vessels is broken down by proteolytic enzymes, and the extracellular matrix in the perivascular space is fragmented. The angiogenic stimuli released thereby caused differentiated endothelial cells which are already present to migrate in the direction of the chemotactic stimulus, during which they simultaneously proliferate and are transformed. Juxta-positioning of endothelial cells then forms new vessel loops with a capillary-type lumen. The onset of synthesis of a new basement membrane follows.

However, recent investigations show that the formation of new blood vessels in the adult organism derives not only from angiogenesis but also from vasculogenic mechanisms. Vasculogenesis means formation of new vessels from endothelial progenitor cells which are differentiating in situ. The belief that vasculogenesis is confined to embryogenesis was refuted by the detection of endothelial progenitor cells (EPC) in peripheral blood of healthy humans and animals. It was possible to prove by using animal models that the endothelial progenitor cells derived from bone marrow are actively involved in neovascularization. It was also shown that a specific CD34-positive subgroup of leukocyte which expresses endothelium-specific antigens becomes established in ischemic regions. In addition, endothelial progenitor cells (EPC) which make a significant contribution to the formation of blood vessels in the adult organism can be obtained from $CD133^+$ and $CD34^{30}$ cells in vitro (Asahara et al., Science, 275 (1997), 964-967; Crosby et al., Circ. Res., 87 (2000), 728-730; Gehling et al., Blood, 95 (2000), 3106-3112). It was additionally shown that injection of isolated $CD34^{30}$ cells or cultivated endothelial progenitor cells expedites restoration of blood flow in diabetic mice (Schatteman et al., J. Clin. Invest., 106 (2000), 571-578) and improves neovascularization in vivo (Asahara et al., Circ. Res., 85 (1999), 221-228; Crosby et al., Circ. Res., 87 (2000), 728-730; Murohara et al., J. Clin. Invest., 105 (2000), 1527-1536). It was moreover possible to show that a neovascularization induced by $CD34^{30}$ cells improves cardiac function (Kocher et al., Nat. Med., 7 (2001), 430-436).

However, the mechanisms underlying the mobilization and differentiation of endothelial progenitor cells are not yet fully explained. Molecular biological and cytobiological investigations indicate that various cytokines and angiogenic growth factors have stimulating effects on the mobilization of endothelial progenitor cells in bone marrow. Thus, it is known that proangiogenic factors such as VEGF and GM-CSF are able to increase the number of endothelial progenitor cells (Asahara et al., EMBO, J., 18 (1999), 3964-3972; Takahashi et al., Nat. Med., 5 (1999), 434-438). VEGF (vascular endothelial growth factor) is a protein which occurs in various isoforms and which binds to the two tyrosine kinase receptors VEGF-R1 (flt-1) and VEGF-R2 (flk-1) which occur for example on the surface of growing endothelial cells (Wernert et al., Angew. Chemie, 21 (1999), 3432-3435). Activation of VEGF receptors leads via the Ras-Raf-MAP kinase pathway to expression of proteinases and specific integrins on the surface of endothelial cells or endothelial progenitor cells and finally to initiation of proliferation and migration of these cells in the direction of the angiogenic stimulus. GM-CSF (granulocyte-macrophage colony-stimulating factor) is a cytokine which was previously known in particular for stimulating white blood corpuscles including neutrophils, macrophages and eosinophils. PlGF (placental growth factor) is known to stimulate the mobilization of endothelial progenitor cells but not proliferation thereof. Investigations by Llevadot et al. (J. Clin. Invest., 108 (2001), 399-405) reveal that HMG-CoA reductase inhibitors, especially statins, which are employed as lipid-lowering medicaments and reduce the morbidity and mortality of coronary disease, are able to mobilize endothelial progenitor cells. Dimmeler et al. (J. Clin. Invest., 108 (2001), 391-397) were able to show further that statins such as atorvastatin and simvastatin significantly improve the differentiation of endothelial progenitor cells in mononuclear cells and $CD34^{30}$ stem cells isolated from peripheral blood in vitro and in vivo. Thus, treatment of mice with statins led to an increased number of differentiated endothelial progenitor cells, with statins showing an effect as strong as that of VEGF.

Stimulation of the mobilization and/or differentiation of endothelial progenitor cells represents an important novel therapeutic strategy for increasing postnatal neovascularization, especially vasculogenesis, and for treating diseases associated with a dysfunction of endothelial progenitor cells and/or endothelial cells.

The present invention is based on the technical problem of providing means and methods for improved stimulation of endothelial progenitor cells and for the therapy of disorders particularly associated with a dysfunction of endothelial progenitor cells.

The present invention solves this technical problem by disclosing the use of erythropoietin and/or its derivatives for stimulating the physiological mobilization of endothelial progenitor cells, the proliferation of endothelial progenitor cells, the differentiation of endothelial progenitor cells to endothelial cells and/or the migration of endothelial progenitor cells in the direction of an angiogenic or vasculogenic stimulus in a human or animal body. The present invention also solves this technical problem by disclosing the use of erythropoietin and/or its derivatives for the therapy of diseases or pathological states associated with a dysfunction of endothelial progenitor cells and/or endothelial cells.

It has surprisingly been found according to the invention that a treatment with erythropoietin leads to physiological mobilization of endothelial progenitor cells, with an increase in the number of circulating endothelial progenitor cells and induction of differentiation thereof, especially in comparatively low EPO doses. In addition, functional deficits, which occur in certain pathological conditions, of the endothelial progenitor cells are compensated. It was possible to show according to the invention that the number of circulating stem cells in patients with chronic kidney disease in the terminal stage is just as high as in healthy subjects, but in these patients they have lost the ability to differentiate to endothelial cells via endothelial progenitor cells. Thus, the number of cells capable of adhesion and showing an endothelial cell phenotype is distinctly reduced in patients with chronic kidney disease compared with healthy subjects. It has now been found according to the invention that the number of circulating stem cells increases significantly by more than 50% after treatment of these patients with erythropoietin. There is moreover a drastic increase in particular in the number of cells which develop an endothelial phenotype. As was demonstrated by means of a functional cell culture assay, there is three-fold increase in the impaired adhesion ability of the endothelial progenitor cells due to erythropoietin treatment in patients with chronic kidney disease. The adhesion ability of differentiating endothelial progenitor cells and of endothelial cells is one of the basic preconditions for the formation of new tissues and/or vessels. Erythropoietin is able in this way to induce neovascularization, in particular vasculogenesis, in tissues or organs in which corresponding vasculogenic or angiogenic stimuli are released.

Erythropoietin (called EPO hereinafter) can be used according to the invention to stimulate the physiological mobilization of endothelial progenitor cells, the proliferation of endothelial progenitor cells, the differentiation of endothelial progenitor cells to endothelial cells and/or for migration of endothelial progenitor cells in the direction of a vasculogenic or angiogenic stimulus in a human or animal body, in particular an adult organism. Erythropoietin can therefore advantageously be employed according to the invention to stimulate the formation of new vessels by vasculogenesis in tissues or organs in which pathological vascular lesions are present. In addition, the formation of endothelial tissue can also be induced owing to the stimulation of endothelial progenitor cells by erythropoietin. Erythropoietin can therefore also be employed according to the invention for treating diseases of the human or animal body which are associated with a dysfunction of endothelial progenitor cells and/or endothelial cells.

In connection with the present invention, "erythropoietin" or "EPO" means a substance which controls the growth or the differentiation and the maturation of stem cells via erythroblasts to erythrocytes. Erythropoietin is a glycoprotein having 166 amino acids, three glycosylation sites and a molecular weight of about 34 000 Da. During EPO-induced differentiation of erythrocyte progenitor cells there is induction of globin synthesis and an increase in the synthesis of the heme complex and in the number of ferritin receptors. The cell can take up more iron and synthesize functional hemoglobin thereby. Hemoglobin binds oxygen in mature erythrocytes. Thus, erythrocytes and the hemoglobin present in them play a key role in the body's oxygen supply. These processes are initiated through the interaction of EPO with an appropriate receptor on the cell surface of erythrocyte progenitor cells (Graber and Krantz, Ann. Rev. Med. 29 (1978), 51-56).

Erythropoietin is produced mainly in the kidney, but also in smaller proportions in the liver and in the brain. Small amounts of erythropoietin are also found in the serum and, under physiological conditions, it is at least partly excreted in the urine. Patients with renal failure are capable of only inadequate erythropoietin (called EPO hereinafter) production and accordingly suffer from anemia. Compensation of erythropoietin deficiency by administering erythropoietin is known. Further clinical applications of erythropoietin are in the administration of erythropoietin for iatrogenic anemia following chemotherapy or radiotherapy of malignant diseases or viral infections (EP 0 456 153 B1). U.S. Pat. No. 4,732,889 discloses the use of erythropoietin-containing compositions for the treatment of anemia associated with rheumatoid arthritis. WO 88/03808 discloses the treatment of hemochromatosis by means of EPO-containing compositions.

The term "erythropoietin" used herein includes EPO of every origin, especially human or animal EPO. The term used herein encompasses not only the naturally occurring, that is wild-type forms of EPO, but also its derivatives, analogs, modifications, muteins, mutants or others, as long as they show the biological effects of wild-type erythropoietin.

In connection with the present invention, "derivatives" mean functional equivalents or derivatives of erythropoietin which are obtained, with retention of the basic erythropoietin structure, by substitution of one or more atoms or molecular groups or radicals, in particular by substitution of sugar chains such as ethylene glycol, and/or whose amino acid sequences differ from that of the naturally occurring human or animal erythropoietin protein in at least one position but essentially have a high degree of homology at the amino acid level and comparable biological activity. Erythropoietin derivatives as can be employed for example in the present invention are disclosed inter alia in WO 94/25055, EP 0 148 605 B1 or WO 95/05465.

"Homology" means in particular a sequence identity of at least 80%, preferably at least 85% and particularly preferably at least more than 90%, 95%, 97% and 99%. The term "homology" which is known to the skilled worker thus refers to the degree of relationship between two or more polypeptide molecules, which is determined by the agreement between the sequences. It is possible in this connection for an agreement to mean both an identical agreement and a conservative amino acid exchange.

The term "derivative" also includes according to the invention fusion proteins in which functional domains of another protein are present on the N-terminal part or on the C-terminal part. In one embodiment of the invention, this other protein may be for example GM-CSF, VEGF, PIGF, a statin or another factor which has a stimulating effect on endothelial progenitor cells. In a further embodiment of the invention, the other protein may also be a factor which has a stimulating effect on differentiated endothelial cells, for example angiogenin or bFGF (basic fibroblast growth factor). It is known that the growth factor bFGF exerts a strong mitogenic and chemotactic activity on endothelial cells.

The differences between an erythropoietin derivative and native erythropoietin may arise for example through mutations such as, for example, deletions, substitutions, insertions, additions, base exchanges and/or recombinations of the nucleotide sequences encoding the erythropoietin amino acid sequences. Obvious possibilities in this connection are also naturally occurring sequence variations, for example sequences from another organism or sequences which have been mutated in a natural way, or mutations introduced deliberately into the erythropoietin-encoding nucleic acid sequences with the aid of conventional means known in the art, for example chemical agents and/or physical agents. In connection with the invention, therefore, the term "derivative" also includes mutation erythropoietin molecules, that is erythropoietin muteins.

It is also possible according to the invention to employ peptide or protein analogs of erythropoietin. In connection with the present invention, the term "analogs" includes compounds which do not have an amino acid sequence identical to the erythropoietin amino acid sequence but whose three-dimensional structure greatly resembles that of erythropoietin and which therefore have a comparable biological activity. Erythropoietin analogs may be, for example, compounds which comprise in a suitable conformation the amino acid residues responsible for the binding of erythropoietin to its receptors and which are therefore able to simulate the essential surface properties of the erythropoietin binding region. Compounds of this type are described for example in Wrighton et al., Science, 273 (1996), 458.

The EPO employed according to the invention can be produced in various ways, for example by isolation from human urine or from the urine or plasma (including serum) of patients suffering from aplastic anemia (Miyake et al., J.B.C. 252 (1977), 5558). Human EPO can be obtained for example also from tissue cultures of human renal cancer cells (JA-OS 55790/1979), from human lymphoblast cells which have the ability to produce human EPO (JA-OS 40411/1982) and from a hybridoma culture obtained by cell fusion of a human cell lines. EPO can also be produced by genetic engineering methods by using suitable DNA or RNA which codes for the appropriate amino acid sequence of EPO to produce the desired protein recombinantly, for example in a bacterium, a yeast, a plant cell line or animal cell line. Methods of these types are described for example in EP 0 148 605 B2 or EP 0 205 564 B2 and EP 0 411 678 B1.

The present invention relates in particular to the use of erythropoietin (called EPO hereinafter) and/or derivatives thereof to stimulate the physiological mobilization of endothelial progenitor cells, the proliferation of endothelial progenitor cells, the differentiation of endothelial progenitor cells to endothelial cells and/or for the migration of endothelial progenitor cells in the direction of a vasculogenic or angiogenic stimulus in a human or animal body, in particular an adult organism.

In connection with the present invention, "endothelial progenitor cells" (EPC) mean cells which circulate in the bloodstream and have the ability to differentiate to endothelial cells. The endothelial progenitor cells which occur during embryonic development are angioblasts. The endothelial progenitor cells occurring in the adult organism are angioblast-like cells which can be obtained from mononuclear cells, in particular $CD34^-CD14^+$ monocytes, and/or $CD34^{30}$ stem cells, which have been isolated from peripheral blood.

In connection with the present invention, "mobilization" or "physiological mobilization" means the process of activating stem cells and/or progenitor cells from the bone marrow by growth factors, with entry of the stem cells or progenitor cells into the bloodstream, in particular into the peripheral blood.

In connection with the present invention "proliferation" means the ability of cells to enlarge and subsequently divide into two or more daughter cells. The EPO-mediated stimulation of endothelial progenitor cells thus relates in particular to the number and thus the dividing behavior of endothelial progenitor cells.

In connection with the present invention, "Differentiation" of endothelial progenitor cells means the development of mononuclear cells derived from the bone marrow via endothelial progenitor cells into endothelial cells. "Endothelial cells" mean the cells which form the endothelium, that is the monolayer cellular lining of vessels and serous cavities. Endothelial cells are characterized in that they release vasoactive substances, for example vasodilating substances such as EDRF (endothelial derived relaxing factor) or constricting substances such as endothelin, factors for inhibition or activation of blood clotting and factors for regulating vascular permeability. Endothelial cells also synthesize components of the subendothelial connective tissue, especially collagens of type IV and V, cell adhesion proteins such as laminin, fibronectin and thrombospondin, growth factors, for example for smooth muscle cells, and factors for the formation of new vessels.

In connection with the present invention, "migration" of endothelial progenitor cells means that the endothelial progenitor cells present in the bloodstream migrate in the direction of a vasculogenic or angiogenic stimulus and become concentrated in the region of the vasculogenic or angiogenic stimulus. A "vasculogenic stimulus" means a chemical stimulus in a tissue or blood vessel of a human or animal body which acts specifically on endothelial progenitor cells and brings about migration thereof to the site in the body from which the chemical stimulus originates. The vasculogenic stimulus induces in this way the vasculogenesis process. An "angiogenic stimulus" means a chemical stimulus in a tissue or blood vessel of a human or animal body which acts specifically on differentiated endothelial cells and brings about migration thereof to the site in the body from which the chemical stimulus originates. The angiogenic stimulus brings about in this way an induction of angiogenesis.

A further embodiment of the invention provides the use of erythropoietin and/or derivatives thereof for increasing the adhesion ability of differentiating endothelial progenitor cells. Erythropoietin is used according to the invention in particular for improving the adhesion ability of endothelial progenitor cells, that is for cell-cell adhesion. The adhesion of differentiating endothelial progenitor cells or differentiated endothelial cells is one of the basic preconditions for the formation of new vessels or of new endothelial tissue. Cell adhesion is mediated by protein molecules.

The present invention also relates to the use of erythropoietin for stimulating the formation of new vessels, in particular stimulation of vasculogenesis. In connection with the present invention, "vasculogenesis" means the formation of new vessels from endothelial progenitor cells which are differentiating in situ. Thus, according to the invention, the use of erythropoietin results in increased involvement of endothelial progenitor cells in the formation of new vessels or in a local formation of new vessels to restore damaged vascular regions. The invention thus provides for the use of erythropoietin and/or its derivatives to promote the formation of new blood vessels and/or the replacement of damaged vascular regions through local formation of new blood vessels.

A further embodiment of the invention provides for the use of erythropoietin and/or derivatives thereof for stimulating endothelial progenitor cells to form endothelial tissue.

A particularly preferred embodiment of the invention provides the use of erythropoietin and/or derivatives thereof for the therapy of pathological states or diseases of the human or animal body which are associated with a dysfunction of endothelial progenitor cells, or of sequelae thereof.

In connection with the present invention, "diseases", "pathological states" or "disorders" mean disturbances of vital processes in organs or in the whole body resulting in subjectively experienced or objectively detectable physical, mental or intellectual changes. The invention is concerned in particular with diseases associated with a dysfunction of endothelial progenitor cells, that is diseases which either are the result of such a dysfunction of these cells or are mediated by these cells. "Sequelae" mean secondary diseases, that is a second disorder added to a primary pathological state.

In connection with the present invention, a "dysfunction" of endothelial progenitor cells means a disturbance of essential cell functions such as metabolic activities, response to stimuli, motility, dividing behavior or differentiation behavior of these cells. A dysfunction of endothelial progenitor cells may consist for example of only inadequate or no proliferation of these cells. Since the proliferation of endothelial progenitor cells is stimulated by the use of erythropoietin, it is thus possible to compensate the deficient dividing behavior both of endothelial progenitor cells and of previously differentiated endothelial cells, and to increase the number of endothelial progenitor cells or endothelial cells. A dysfunction of endothelial progenitor cells may consist for example of the impaired ability of these cells to differentiate to endothelial cells. The dysfunction of endothelial progenitor cells may also be caused by their impaired adhesion ability and/or their impaired ability to migrate in the direction of an angiogenic or vasculogenic stimulus. Such dysfunctions of endothelial progenitor cells may lead for example to the impairment or prevention of the formation of new endothelial tissue and/or vasculogenesis. A dysfunction of endothelial progenitor cells may also have a pathogenic cause, for example due to hypertension, hyperlipoproteinemia, uremia or diabetes. The dysfunction of endothelial progenitor cells may be manifested for example by a reduced production of NO (=EDRF) by NO synthases (NOS) from L-arginine, increased endothelin production and/or enhanced production of adhesion molecules such as ICAM-1 and VCAM-1.

The diseases associated with a dysfunction of endothelial progenitor cells are according to the invention in particular hypercholesterolemia, diabetes mellitus, endothelium-mediated chronic inflammatory disorders such as inflammations of vessels, endotheliosis including reticuloendotheliosis, atherosclerosis, coronary heart disease, myocardial ischemia, angina pectoris, age-related cardiovascular disorder, ischemic disorders of the extremities, Raynaud's disease, preeclampsia, pregnancy-induced hypertension, chronic or acute renal failure, especially terminal renal failure, heart failure, wound healing and sequelae thereof.

"Hypercholesterolemia" is characterized by elevated concentrations of cholesterol in the blood. By far the commonest form of primary hypercholesterolemia is polygenic hypercholesterolemia. Secondary hypercholesterolemias frequently occur in association with diabetes mellitus, nephrotic syndrome, hypothyroidism and hepatic disorders.

"Diabetes mellitus" encompasses various forms of glucose metabolism disorders differing in etiology and symptoms. Responsible for the development of vessel-related diabetic complications is, in particular, the AGE-RAGE system. AGEs (advanced glycation endproducts) are produced by a series of complex reactions after long-lasting exposure of proteins or lipids to reducing sugars, for example glucose. The formation of AGEs takes place during the normal aging process and to an increased extent in diabetes mellitus and Alzheimer's disease. Binding of AGEs leads to oxidative stress, activation of the NF-κB transcription factor and thus a disturbance of endothelial homeostasis.

"Endothelium-mediated chronic inflammatory disorders" are disorders or conditions of a human or animal body which derive from a defense response of the body and its tissues to harmful stimuli, with certain signal molecules altering the properties of endothelial cells so that, in concert with the activation of other cell types, leukocytes remain adherent to endothelial cells, finally penetrate into the tissue and there initiate inflammation. One example of an endothelium-mediated inflammation is leukocytic vasculitis. A central part is played in the activation of an endothelium-mediated inflammatory event by the transcription factor NF-κB. Another system leading to the development of endothelial cell-mediated chronic inflammations is the AGE-RAGE system.

"Endotheliosis" means degenerative and proliferative endothelial changes associated with non-thrombopenic purpura. "Reticuloendotheliosis" means diseases of the reticulohistiocytic system, such as reticulum, reticulosis, reticulohistiocytosis and Hand-Schüller-Christian disease.

"Myocardial ischemia" means bloodlessness or hypoperfusion, that is an impairment of the blood supply, of the muscular wall of the heart as a result of inadequate or absent arterial supply of blood. A "cardiac infarct" or "myocardial infarct" is a necrosis of a localized region of the myocardium, which usually occurs as an acute event complicating chronic coronary heart disease. "Coronary heart disease" or "ischemic heart disease" is a degenerative coronary disorder which, owing to a constriction or a closure of coronary vessels of the heart, leads to a reduced blood supply to the myocardium. "angina pectoris" means an acute coronary insufficiency or stenocardia which may be induced by an imbalance of the oxygen supply and oxygen demand associated with coronary heart disease, coronary spasms, impairments of blood flow, cardiac arrhythmias, hypertension or hypotension. "Raynaud's disease" means ischemic states which are caused by vasoconstriction, that is vessel spasms, and occurs episodically, usually in the arteries of the fingers. Primary Raynaud's disease is a purely functional impairment of the small vessels supplying the distal parts of the extremities, whereas secondary Rynaud's disease has another disease underlying it, for example an inflammation of vessels.

"Preeclampsia" is an endothelial and vascular disease of the maternal body and appears to be the effect of endotheliotropic substances from the placenta. Preeclampsia is a multisystem disorder which may lead to disturbances of function of numerous organs and be manifested by diverse symptoms. The impairments of blood supply which are typical of the disorder are the result of an increased vascular resistance, possibly with local variations in severity. It is regarded as confirmed that an endothelial dysfunction is the central component of the pathogenesis of preeclampsia.

"Renal failure" means in connection with the present invention the restricted ability of the kidneys to excrete substances normally excreted in the urine, and in advanced stages there is also loss of the ability to regulate the electrolyte, water and acid-base balance. Terminal renal failure is characterized by a collapse of the excretory and endocrine function of the kidneys.

The renal failure may according to the invention be acute renal failure which is also referred to as acute kidney failure or shock aneuria. Acute renal failure is characterized by a sudden partial or complete loss of the excretory function of the kidneys as a result of usually reversible kidney damage. The cause may be hypoperfusion due to hypovolemia, hypotension and dehydration resulting from blood losses (polytrauma, gastrointestinal or postpartum bleeding, major surgical procedures on the heart, vessels, abdomen or prostate), shock (myocardial infarct, embolism), serious infections (sepsis, peritonitis, cholecystitis), hemolysis (hemolytic-uremic syndrome, paroxysmal hemoglobulinuria, transfusion reaction), myolysis (crush syndrome, rhabdomyolysis, myositis, burns), water and electrolyte losses (massive vomiting, diarrhea, excessive sweating, ileus, acute pancreatitis). Further causes may be nephrotoxins such as exogenous toxins, for example aniline, glycol compounds, methanol and the like, or endogenous toxins, for example myoglobin and oxalates. Further causes of acute renal failure are renal diseases, for example inflammatory nephropathies or rejection reactions following renal transplantation. Acute renal failure may also be caused by retention of urine following obstruction to the flow of urine. The treatment according to the invention of acute renal failure with erythropoietin leads according to the invention to prevention or at least diminution of progression of acute renal failure.

The renal failure may according to the invention also be chronic renal failure. Causes of chronic renal failure are vascular, glomerular and tubulointerstitial renal disorders, infections and inborn or acquired structural defects. Causes of chronic renal failure are, inter alia, chronic glomerulopathy, chronic pyelonephritis, analgesic nephropathy, obstructive uropathy and arterio- and arteriolosclerosis. The terminal stage of chronic renal failure is uremia. The treatment according to the invention of chronic renal failure with erythropoietin leads according to the invention to a diminution in the progression of chronic renal failure.

In connection with the present invention, "heart failure" means a pathological state which is also referred to as myocardial insufficiency or weakness of the heart muscle. Heart failure is characterized by inadequate functioning of the heart, the heart no longer being capable of efficient delivery to comply with the requirements. Heart failure can be categorized according to various aspects. For example, according to the affected segment of the heart it is classified as right heart failure, left heart failure and failure on both sides (global failure). According to the stability of an equilibrium influenced by physiological and therapeutic mechanisms, a distinction is made between compensated and decompensated heart failure. Classification takes place into acute and chronic heart failure according to the time course. Causes of heart failure are, inter alia, myocardial infarction, cardiomyopathy, inborn or acquired cardiac defects, essential or pulmonary hypertension, cardiac arrhythmias, coronary heart disease or myocarditis.

In connection with the present invention, "wound healing" means the physiological processes for regenerating damaged tissue and for closing a wound, especially formation of new connective tissue and capillaries. The wound healing may be primary wound healing (first intention healing), which is characterized by rapid and complication-free closure and substantially complete recovery as a result of minimal formation of new connective tissue between the edges of a wound, which have a good blood supply and are approximated where appropriate, of a clean wound. Wounds where the edges of the wound are further apart and, in particular, crushed or necrotic, and infected wounds, undergo delayed secondary wound healing (second intention healing) in which, as a result of an (a)bacterial inflammation, there is filling of the tissue defect with granulation tissue and extensive formation of scar tissue. Epithelialization starting from the edge terminates the wound healing. The wound healing is divided into three phases, namely latency phase, proliferative phase and repair phase. The latency phase in turn is divided into the oxidative phase with scab formation, especially in the first few hours after the wound occurred, and the absorptive phase with catabolic autolysis, which extends over a period of from one to three days after the wound occurred. The proliferative phase is characterized by anabolic repair with production of collagen by fibroblasts and occurs on the fourth to seventh day after the wound occurred. The repair phase occurs after the eighth day after the wound occurred and is characterized by transformation of the granulation tissue into a scar.

A "wound" means in connection with the present invention an interruption of the coherence of body tissues with or without loss of substance and caused by mechanical injury or physically caused cell damage. Types of wound are mechanical wounds, thermal wounds, chemical wounds, radiation wounds and disease-related wounds. Mechanical wounds arise through traumatic violence and occur in particular as incision and puncture wounds, crushing, lacerating, tearing and abrading wounds, scratch and bite wounds and projective wounds. Thermal wounds arise through exposure to heat or cold. Chemical wounds arise in particular through the action of acids or alkalis. Radiation wounds arise for example through exposure to actinic and ionizing radiation. Wounds occurring in relation to disease are in particular congestion-related wounds, traumatic wounds, diabetic wounds etc. The invention provides in particular for erythropoietin to be administered preferably topically or intravenously for wound healing.

The present invention therefore relates to the use of erythropoietin for the therapy of hypercholesterolemia, diabetes mellitus, endothelium-mediated chronic inflammatory disorders, endotheliosis including reticuloendotheliosis, atherosclerosis, coronary heart disease, myocardial ischemia, angina pectoris, age-related cardiovascular disorders, ischemic disorders of the extremities, preeclampsia, Raynaud's disease, pregnancy-induced hypertension, chronic or acute renal failure, especially terminal renal failure, heart failure, wound healing and sequelae thereof.

The invention provides for erythropoietin to be administered to a patient in a therapeutically effective dose which is sufficient to cure the condition of an aforementioned disease, in particular a disease associated with a dysfunction of endothelial progenitor cells, or to prevent this condition, to stop the progression of such a disease and/or to alleviate the symptoms of such a disease. The dose to be administered to a patient depends on many factors, for example the age, body weight and gender of the patient, the severity of the disorders etc.

It is particularly preferred according to the invention for erythropoietin, in all the uses, methods and compositions of the present disclosure, to be used in very small amounts which are below the amounts known to be employed, administering in particular in vivo, i.e. per patient, EPO doses of from 200 to 2 000 units (IU; international units)/week, preferably doses of from 500 to 2 000 IU/week, depending on the severity of the disorder and depending on renal function. The doses, provided according to the invention, of from 200 to 2

000 units (IU)/week and per patient, especially from 500 to 2 000 IU/week and per patient, are subpolycythemic doses, that is doses which do not lead to erythrocytes with hematocrit values of more than 50%. The subpolycythemic doses provided according to the invention correspond to weekly doses of about 1 to 90 units (IU) of EPO/kg of body weight, in particular 1 to 45 IU of EPO/kg of body weight, or a comparable weekly dose of Aranesp of from 0.005 to 0.45 μg/kg of body weight, in particular 0.005 to 0.225 μg/kg of body weight. Aranesp is a doubly PEGylated EPO. The dose of from 200 to 2 000 units/week per patient, in particular from 500 to 2 000 IU/week and per patient, which is provided according to the invention for the treatment of diseases or pathological states associated with a dysfunction of endothelial progenitor cells is very low compared with the initial dose of 50-150 IU/kg of body weight/week (usually starting with 4 000-8 000 IU/week, but also considerably higher if the result of therapy is unsatisfactory) normally employed for the therapy of renal anemia.

A particularly preferred embodiment of the invention relates to the use of erythropoietin and/or its derivative as active ingredient for producing a pharmaceutical composition or a medicament for the therapy of pathological states or diseases associated with a dysfunction of endothelial progenitor cells.

An "active ingredient" means according to the invention an endogenous or exogenous substance which on contact with target molecules or target cells or target tissues influences in a differentiated manner specific functions of tissues, organs or organisms. The invention thus provides for erythropoietin as active ingredient of the pharmaceutical composition of the invention influencing the proliferation, differentiation and/or migration behavior of endothelial progenitor cells on contact therewith in a human or animal organism in such a way that dysfunctions of endothelial progenitor cells can be compensated and the diseases occurring as a consequence of these dysfunctions effectively controlled, alleviated or eliminated, or these diseases effectively prevented.

In connection with the present invention, a "pharmaceutical composition" or a "medicament" means a mixture which is used for diagnostic, therapeutic and/or prophylactic purposes, that is promoting or restoring the health of a human or animal body, and which includes at least one natural or synthetically produced active ingredient which brings about the therapeutic effect. The pharmaceutical composition may be either a solid or a liquid mixture. For example, a pharmaceutical composition including the active ingredient may comprise one or more pharmaceutically acceptable components. The pharmaceutical composition may additionally include additives normally used in the art, for example stabilizers, manufacturing materials, release agents, disintegrants, emulsifiers or other substances normally used for pharmaceutical composition production.

The invention provides in particular the use of erythropoietin and/or a derivative thereof as active ingredient for producing a medicament for the therapy of hypercholesterolemia, diabetes mellitus, endothelium-mediated chronic inflammatory disorders such as inflammations of vessels, endotheliosis including reticuloendotheliosis, atherosclerosis, coronary heart disease, myocardial ischemia, angina pectoris, age-related cardiovascular disorder, ischemic disorders of the extremities, Raynaud's disease, preeclampsia, pregnancy-induced hypertension, acute or chronic renal failure, especially terminal renal failure, heart failure, wound healing and sequelae thereof.

The pharmaceutical composition of the invention may be suitable both for topical and for systemic administration.

A preferred embodiment of the invention provides for the pharmaceutical composition to be used for parenteral, in particular intravenous, intramuscular, intracutaneous or subcutaneous administration. The erythropoietin-containing medicament preferably has the form of an injection or infusion.

A further use provides for the erythropoietin-containing pharmaceutical composition to be administered orally. For example, the erythropoietin-containing medicament is administered in a liquid dosage form such as a solution, suspension or emulsion, or a solid dosage form such as a tablet.

A further use provides for the pharmaceutical composition to be suitable for pulmonary administration or for inhalation. The invention thus provides for erythropoietin to be administered in a therapeutically effective manner directly onto the lungs of the patient. This type of administration of erythropoietin makes it possible to deliver an erythropoietin dose quickly to a patient without the need to perform an injection. When erythropoietin is absorbed through the lungs it is possible to deliver considerable amounts of erythropoietin via the lungs to the bloodstream, which leads to increased amounts of erythropoietin in the bloodstream. In a preferred embodiment of the invention, the pharmaceutical composition to be absorbed through the lung is an aqueous or nonaqueous solution or a dry powder. When the erythropoietin-containing medicament to be administered by the pulmonary route is in the form of a dry powder, the latter preferably includes erythropoietin-containing particles, where the particles have a diameter of less than 10 μm, so that the medicament can also reach distal regions of the patient's lung. A particularly preferred embodiment of the invention provides for the medicament which is to be administered by the pulmonary route to be in the form of an aerosol.

A particularly preferred embodiment of the invention relates to the use of erythropoietin for producing a pharmaceutical composition for the therapy of diseases associated with a dysfunction of endothelial progenitor cells, where the pharmaceutical composition comprises besides erythropoietin as active ingredient at least one further additional active ingredient to stimulate endothelial progenitor cells.

The further active ingredient is preferably an active ingredient which stimulates in particular the physiological mobilization of endothelial progenitor cells from the bone marrow. However, the further active ingredient may also be according to the invention an active ingredient which stimulates in particular the dividing behavior, that is the proliferation, of endothelial progenitor cells. However, there is also the possibility according to the invention for the further active ingredient in particular to stimulate the differentiation behavior and/or the migration behavior of endothelial progenitor cells. The further active ingredient which stimulates endothelial progenitor cells is particularly preferably VEGF, PIGF, GM-CSF, an HMG-CoA reductase inhibitor, in particular a statin such as simvastatin, mevastatin or atorvastatin, and/or an NO donor, especially L-arginine.

The invention also provides for the at least one further active ingredient in particular to stimulate differentiated endothelial cells, that is the proliferation and/or migration thereof, but not endothelial progenitor cells. Particular preference is given in this connection to bFGF (basic fibroblast growth factor) or angiogenin.

A further embodiment of the invention relates to the use of erythropoietin and/or derivatives thereof as active ingredient for producing a pharmaceutical composition to stimulate endothelial progenitor cells, in particular to stimulate the mobilization, proliferation, differentiation to endothelial cells and/or for migration in the direction of a vasculogenic or angiogenic stimulus. The invention further provides for the use of erythropoietin and/or its derivatives as active ingredient for producing a pharmaceutical composition to stimulate vasculogenesis and/or endothelium formation, in particular in the adult human or animal organism.

The present invention therefore also relates to pharmaceutical compositions to stimulate endothelial progenitor cells, in particular to stimulate the mobilization, proliferation, differentiation thereof to endothelial cells and/or migration in the direction of a vasculogenic or angiogenic stimulus, to stimulate vasculogenesis and/or endothelium formation and for the treatment of disease of the human or animal body which are associated with a dysfunction of endothelial progenitor cells and/or endothelial cells. The present invention relates in particular to pharmaceutical compositions or medicaments which include erythropoietin as active ingredient and at least one further active ingredient to stimulate endothelial progenitor cells and/or differentiated endothelial cells. In a preferred embodiment, the present invention relates to pharmaceutical compositions which include erythropoietin and at least one further active ingredient from the group consisting of VEGF, PIGF, GM-CSF, an HMG-CoA reductase inhibitor, in particular a statin such as simvastatin, mevastatin or atorvastatin, an NO donor, especially L-arginine, bFGF and angiogenin.

A further preferred embodiment of the invention relates to the use of erythropoietin for producing a transplantable endothelial cell preparation. The invention provides in this connection in particular for endothelial cells to be produced in vitro by cultivating endothelial progenitor cells in the presence of erythropoietin and subsequently transplanted into a recipient organism, in particular an organism suffering from a disease associated with a dysfunction of endothelial progenitor cells. For example, mononuclear cells (MNC) can be isolated from blood by density gradient centrifugation and cultivated in suitable culture media in vitro. Methods for the isolation and in vitro cultivation of mononuclear cells are described for example in Asahara, Science, 275 (1997), 964-967; Dimmeler et al., J. Clin. Invest., 108 (2001), 391-397 and Llevadot et al., J. Clin. Invest., 108 (2001) 399-405. The mononuclear cells are then cultivated further in the presence of erythropoietin in order to stimulate the proliferation and differentiation behavior of the endothelial progenitor cells present in the MNCs, and in particular to increase the number of differentiated adherent endothelial cells. The invention also provides for the cultivation of the MNCs to take place in the presence of erythropoietin and at least one further substance which stimulates the proliferation and differentiation of endothelial progenitor cells. The further substance particularly preferably employed is VEGF, PIGF, GM-CSF, an NO donor such as L-arginine or an HMG-CoA reductase inhibitor such as a statin, in particular simvastatin, mevastatin or atorvastatin.

A further preferred embodiment of the invention provides for the use of erythropoietin for the pretreatment and/or further treatment of tissues or organs to be transplanted. In this case, the transplants are treated with erythropoietin before the transplantation, preferably immediately before, while still in the donor organism. The recipient organism can likewise be treated with erythropoietin from the time of transplantation onwards. This treatment of the organs or tissues to be transplanted, both directly before and after transplantation, with erythropoietin achieves according to the invention rapid formation of new blood vessels in the transplant after transplantation has taken place into a body, because of the induced vasculogenesis, and rapid connection of these newly formed blood vessels to the blood system of the recipient organism.

The formation of endothelia is likewise achieved quickly in this way. The treatment of organ or tissue transplants with erythropoietin thus brings about faster incorporation of these systems in the body, thus considerably reducing the risk of rejection.

A further development of the invention provides for the organ or tissue transplants to be treated before transplantation with erythropoietin in combination with at least one further factor which stimulates endothelial progenitor cells. This factor is preferably a substance from the group consisting of VEGF, PIGF, GM-CSF, an HMG-CoA reductase inhibitor, for example a statin, in particular simvastatin, mevastatin or atorvastatin, or an NO donor, in particular L-arginine. A further development provides for the organ or tissue transplants to be treated before transplantation besides erythropoietin with a further substance which stimulates the proliferation and migration of differentiated endothelial cells. This substance is particularly preferably angiogenin or bFGF. A further development provides for the pretreatment of the organ or tissue transplants with erythropoietin to take place using isolated and, where appropriate, in vitro expanded endothelial progenitor cells.

A further particularly preferred embodiment of the invention provides for erythropoietin to be used to produce implantable or transplantable cell-containing in vitro organs or tissues. The invention provides in particular for the organ or tissue produced in vitro to be treated before the transplantation or implantation with erythropoietin in vitro in order to stimulate endothelial progenitor cells which are present in the body of the recipient organism, especially the physiological mobilization, migration, proliferation and differentiation thereof. The recipient organism is preferably treated further, after transplantation or implantation of the in vitro organ or tissue, with erythropoietin in the doses of the invention. Treatment of the in vitro organ or tissue before transplantation or implantation with erythropoietin and, where appropriate, subsequent treatment of the recipient organism with erythropoietin achieves according to the invention rapid formation of new blood vessels in the in vitro organ or tissue system after transplantation or implantation has taken place into a body, because of the induced vasculogenesis, and rapid connection of these newly formed blood vessels to the blood system of the recipient organism. Rapid formation of endothelia and thus reendothelialization is likewise achieved in this way. Treatment of the in vitro organ or tissue systems with erythropoietin thus brings about faster incorporation of these systems into the body, thus considerably reducing the risk of rejection, and serves to protect the transplant.

An "in vitro organ or tissue system" means a transplantable or implantable cell-containing tissue or organ which is produced in vitro using defined cells and/or defined tissues and under defined culture conditions. An "implantable in vitro organ or tissue system" means a system which, besides cells, includes exogenous materials. A "transplantable in vitro organ or tissue system" means in particular a cell-containing system which, besides cells, tissue or organs of the same or a different individual, comprises endogenous substances. In vitro organs or tissues are characterized in particular by substantially corresponding in terms of their structure to the native organs or tissues which are to be replaced, and thus are able to undertake the function of the replaced native organs or tissues in vivo.

One development of the invention provides for the in vitro organ or tissue systems to be treated before transplantation or implantation with erythropoietin in combination with at least one further factor which stimulates endothelial progenitor cells. This factor is preferably a substance from the group consisting of VEGF, PlGF, GM-CSF, an HMG-CoA reductase inhibitor, in particular simvastatin, mevastatin or atorvastatin, and an NO donor. A further development provides for the in vitro organ or tissue systems to be treated before transplantation or implantation besides erythropoietin with a further substance which stimulates the proliferation and migration of differentiated endothelial cells. This substance is particularly preferably angiogenin or bFGF. A further development provides for the in vitro organ or tissue systems additionally to comprise isolated and, where appropriate, in vitro expanded endothelial progenitor cells.

A further preferred embodiment of the invention relates to the use of erythropoietin for producing vascular prostheses or heart valves, where the vascular prostheses or heart valves are coated with erythropoietin before insertion into a body, in particular a human body. The coating of the vascular prostheses or heart valves with erythropoietin achieves stimulation of endothelial progenitor cells in the body of the recipient organism, stimulating in particular their mobilization from the bone marrow, their proliferation, their differentiation to endothelial cells and their migration to the employed vascular prostheses or heart valves. Following introduction of the vascular prosthesis or heart valves produced in this way into a body, the latter can be treated further with erythropoietin, in particular in the doses of the invention. This results in faster formation of endothelial layers on the employed vascular prostheses and thus faster incorporation into the relevant area of the body. A preferred development provides for additionally employed isolated and, where appropriate, in vitro expanded endothelial progenitor cells for coating the vascular prostheses and heart valves.

The present invention likewise relates to a method for stimulating endothelial cell formation in vitro comprising a) isolation of cell populations comprising endothelial progenitor cells from blood by means of density gradient centrifugation b) cultivation of the isolated cell populations comprising endothelial progenitor cells in cell culture medium, and c) cultivation of the cell populations in the presence of erythropoietin.

The cultivation of the cell populations can according to the invention take place in the presence of a further substance which stimulates endothelial progenitor cells.

The present invention further relates to a method for treating diseases associated with a dysfunction of endothelial progenitor cells by administering erythropoietin in a dose of from 200 to 2 000 IU/week, in particular in a dose of from 500 to 2 000 IU/week, to a patient with such a disease. The method of the invention is particularly suitable for treating diseases of the human body such as hypercholesterolemia, diabetes mellitus, endothelium-mediated chronic inflammatory disorders such as inflammations of vessels, endotheliosis including reticuloendotheliosis, atherosclerosis, coronary heart disease, myocardial ischemia, angina pectoris, age-related cardiovascular disorder, ischemic disorders of the extremities, Raynaud's disease, preeclampsia, pregnancy-induced hypertension, acute or chronic renal failure, especially terminal renal failure, heart failure, wound healing and sequelae.

A preferred embodiment of the method of the invention for treating diseases associated with a dysfunction of endothelial progenitor cells provides for administration to the patient besides erythropoietin of at least one further active ingredient selected from the group consisting of VEGF, PlGF, GM-CSF, an HMG-CoA reductase inhibitor and an NO donor. The HMG-CoA reductase inhibitor which is administered is preferably a statin such as simvastatin, mevastatin or atorvastatin. The NO donor which is administered is preferably L-arginine.

A further preferred embodiment of the method of the invention for treating diseases associated with a dysfunction of endothelial progenitor cells provides for endothelial progenitor cells to be isolated from the blood of a human organism, to be expanded in vitro using erythropoietin and to be differentiated to endothelial cells and, after purification and isolation of the differentiated endothelial cells or the differentiating endothelial progenitor cells, the latter then to be transplanted in a targeted manner into a region of the body, a tissue or an organ of a patient which is damaged owing to the dysfunction of endothelial progenitor cells and/or endothelial cells, in order to induce local formation of new endothelium there. A more targeted and faster treatment of the damaged regions of the body, tissues and/or organs of the patient is possible in this way. This embodiment of the method of the invention for treating diseases associated with a dysfunction of endothelial progenitor cells comprises the following steps:

a) isolation of cell populations comprising endothelial progenitor cells from blood by means of density gradient centrifugation, b) cultivation of the cell populations comprising endothelial progenitor cells in cell culture medium, c) cultivation of the cell populations comprising endothelial progenitor cells in the presence of erythropoietin to stimulate the proliferation of endothelial progenitor cells and/or differentiation thereof to endothelial cells, d) isolation and purification of the differentiated endothelial cells, and e) transplantation of the differentiated endothelial cells into a body with a disease associated with a dysfunction of endothelial progenitor cells.

Following transplantation of the differentiated endothelial cells into a body, the latter can be treated further with erythropoietin, in particular in the doses of from 200 to 2 000 IU/week provided according to the invention.

It is possible according to the invention for the cell populations comprising endothelial progenitor cells to be cultivated in vitro in the presence of at least one further active ingredient selected from the group consisting of VEGF, PlGF, GM-CSF, an HMG-CoA reductase inhibitor and an NO donor. The HMG-CoA reductase inhibitor used for the cultivation is preferably a statin such as simvastatin, mevastatin or atorvastatin.

A further preferred embodiment of the invention relates to a method for treating vascular disorders, comprising:

a) isolation of cell populations comprising endothelial progenitor cells from blood by means of density gradient centrifugation, b) cultivation of the cell populations comprising endothelial progenitor cells in cell culture medium, c) cultivation of the cell populations comprising endothelial progenitor cells in the presence of erythropoietin to stimulate the proliferation of endothelial progenitor cells and/or differentiation thereof to endothelial cells, d) isolation and purification of the differentiated endothelial cells, and e) transplantation of the endothelial cells into a body with a vascular disorder.

Following transplantation of the endothelial cells into the body with a vascular disorder, the latter can be treated further with erythropoietin, preferably in the doses of the invention of from 200 IU/week to 2 000 IU/week.

It is possible according to the invention for the cell populations comprising endothelial progenitor cells to be cultivated in the presence of at least one further active ingredient selected from the group consisting of VEGF, PIGF, GM-CSF and/or an HMG-CoA reductase inhibitor. The HMG-CoA reductase inhibitor used for the cultivation is preferably a statin such as simvastatin, mevastatin or atorvastatin.

The method of the invention for treating vascular disorders thus provides for endothelial progenitor cells to be isolated from the blood of a human organism, to be expanded in vitro using erythropoietin and to be differentiated to endothelial cells and, after purification and isolation of the differentiated endothelial cells or the differentiating endothelial progenitor cells, the latter then to be transplanted in a targeted manner into a damaged blood vessel or an ischemic region in order to induce local neovascularization there. More targeted and faster treatment of damaged blood vessels or ischemic tissues is possible in this way. The method of the invention for treating vascular disorders is particularly suitable for treating vascular disorders such as ischemia, especially cerebral ischemia, ischemic disorders of the extremities, myocardial ischemia, myocardial infarction, stroke, coronary heart disease, angina pectoris, acute arterial occlusion, arterial occlusive disease, Raynaud's disease and ergotism.

Further advantageous developments of the invention are evident from the dependent claims.

The invention is explained in more detail by means of the following figures and examples.

FIG. 1 shows the results of a FACS analysis of circulating $CD34^{30}$ stem cells (cSC). (A-D): patients' samples; (E-F): isotype controls. cSC were identified by means of the additional expression of the CD34 marker (B and F), by means of the characteristic low to moderate CD45 antigen expression (C and G) and by means of the characteristic light scattering properties (D and H). The absolute cSC number was calculated per 100 000 monocytes and lymphocytes.

FIG. 2 shows a quantitative determination of circulating stem cells by means of flow cytometry. The figure shows the time-dependent effect of erythropoietin treatment using rhEPO (recombinant human erythropoietin) after 0, 2, 4, 6 and 8 weeks. n=11, the values correspond to averages +/− standard deviation. Medians depicted as line.

*: $p<0.01$ compared with 2 weeks; □.□.$p<0.05$ compared with 4 weeks, #: $p<0.05$ compared with 8 weeks.

FIG. 3 shows a quantitative determination of cultivated endothelial progenitor cells (EPC). The figure shows that rhEPO treatment increases the relative number of EPCs. EPCs were isolated before the treatment of renal patients with rhEPO and 2, 4, 6 and 8 weeks after treatment of the patients with rhEPO, and characterized by means of their adhesion ability and the two markers acLDL-Dil and UEA-1 FITC. n=11, the values correspond to averages +/− standard deviation. Medians depicted as line.

*: $p<0.01$ compared with the period before treatment;
: $p<0.001$ compared with the period before treatment.

FIG. 4 shows the quantitative determination of cultivated endothelial progenitor cells (EPC). The figure shows that the absolute number of EPCs before initiation of rhEPO therapy is significantly reduced compared with healthy age- and gender-matched subjects. Patients with renal anemia thus show distinct EPC dysfunction compared with control subjects. This reduced number of functional EPC was compensated 8 weeks after starting rhEPO therapy for renal anemia. EPCs were isolated before the treatment of renal patients with rhEPO and 2, 4, 6 and 8 weeks after treatment of the patients with rhEPO, and characterized by means of their adhesion ability and the two markers acLDL-Dil and UEA-1 FITC. n=11. The example shown is the course over 8 weeks and all the controls. The absolute values are shown on the one hand as individual values. In addition, box plots are shown (90th/75th/50th/25th and 10th percentiles and the average). Age- and gender-matched subjects for which EPCs were isolated and characterized analogously (n=11) served as healthy control.

FIG. 5 shows the effect of erythropoietin on wound healing. The figure shows that on treatment of a standardized skin wound on mice, made with a tissue punch, with erythropoietin the wound was completely closed only after 7 to 8 days, whereas on treatment of the wound with physiological sodium chloride solution (saline) the wound was not completely closed until after 13 to 14 days. Treatment with erythropoietin or physiological sodium chloride solution started 7 days before making the skin wound. Recombinant human erythropoietin was administered once a week by s.c. (subcutaneous) injection (0.1 μg/kg Aranesp) (n=5 per group).

FIG. 6 shows that erythropoietin diminishes the loss of renal function after acute kidney failure (acute renal failure). Sprague Dawley rats (250-300 g) were included in the study. The rats were anesthetized with ketamine (120 mg/kg) and Rompun (10 mg/kg). One of the experimental groups received Aranesp 0.1 μg/kg of body weight once on the day before induction of the acute kidney failure. The comparison group comprised experimental animals each given an s.c. injection of sodium chloride at the same time. Blood flow into the kidney was stopped for 45 minutes by placing an arterial clamp on the right renal arteries. A left nephrectomy was performed in this time. A sham operation was performed on a further control group. This entailed opening the abdomen, exposing the left renal artery but not stopping the blood supply, and removing the contralateral right kidney. All the animals were anesthetized for 60 min and sacrificed 24 h after the operation. The 45-minute ischemia with subsequent reperfusion of the remaining right kidney led to an extensive acute loss of renal function in the animals treated with sodium chloride. This is reflected by a serum creatinine level 24 h after the ischemia-reperfusion which is 7 times higher than the level before the ischemia-reperfusion ($p<0.05$). By contrast, the animals treated with erythropoietin analog Aranesp showed only a four-fold increase in the serum creatinine levels one day after induction of the ischemia-reperfusion damage. There was no increase in the retention levels in the animals which underwent left nephrectomy and a sham operation on the right kidney. The figure shows the creatinine concentration in the serum of EPO-treated animals (IR+EPO), NaCl-treated animals (IR) and sham-operated animals (sham OP) before ischemia-reperfusion (IR) injury and 24 hours thereafter. It is evident from the figure that the serum creatinine concentration in the Aranesp-treated animals is almost halved compared with the control without (NaCl treatment) 24 hours after ischemia-reperfusion injury.

FIG. 7 shows the Kaplan-Mayer survival plots of two experimental groups treated either with Aranesp or NaCl after induction of chronic renal failure. 8-week old Sprague Dawley rats were included in the study. The rats were anesthetized with ketamine (120 mg/kg) and Rompun (10 mg/kg). The right kidney was removed from them on day 0 and, immediately after removal, was fixed in formalin for histological examination. The segmental arteries which supply the upper and lower renal pole of the left kidney were ligated. This results in a renal infarction of the corresponding areas of the kidney, and only the middle third of the kidney retains its function. The rats received s.c. injection of Aranesp (0.1 μg/kg of body weight) or NaCl once a week. The animals treated with the erythropoietin analog Aranesp show a significant survival advantage compared with the animals treated with sodium chloride ($p=0.027$; log rank test).

FIGS. 8-15 show optical microscopic kidney sections 6 weeks after induction of chronic renal failure in two experimental groups which were treated either with Aranesp or NaCl and whose Kaplan-Mayer survival plots are depicted in FIG. 7.

FIG. 8 shows the histological changes in a Sprague-Dawley rat with chronic renal failure after NaCl treatment once a week starting immediately after induction of the chronic renal failure for a period of 6 weeks. The chronic renal failure results from removal of the right kidney and ligation of the segmental arteries which supply the upper and lower renal pole of the left kidney. The figure shows a medium-sized preglomerular artery with characteristic onion ring-type vessel wall proliferation associated with severe hypertensive damage, called Fahr's malignant nephrosclerosis with endarteritis.

FIG. 9 shows the histological changes in a Sprague-Dawley rat with chronic renal failure after NaCl treatment once a week starting immediately after induction of the chronic renal failure for a period of 6 weeks. The chronic renal failure results from removal of the right kidney and ligation of the segmental arteries which supply the upper and lower renal pole of the left kidney. The figure shows florid focal-segmental glomerulosclerosis, called proliferative FSGS (right glomerulus). The other glomerulus (left) shows ischemic collapse of the loop convolution. A small vessel with severe endothelial damage is to be seen lower in the picture. The observed histological changes correspond to hypertensive organ damage or changes associated with overload nephropathy following 5/6 nephrectomy.

FIG. 10 shows the histological changes in a Sprague-Dawley rat with chronic renal failure after NaCl treatment once a week starting immediately after induction of the chronic renal failure for a period of 6 weeks. The chronic renal failure results from removal of the right kidney and ligation of the segmental arteries which supply the upper and lower renal pole of the left kidney. The figure shows almost complete sclerosis or destruction of a glomerulus with compensatory enlargement and pronounced hyalinosis or fibrinoid necrosis of the relevant afferent arterioles.

FIG. 11 shows the histological changes in a Sprague-Dawley rat with chronic renal failure after NaCl treatment once a week starting immediately after induction of the chronic renal failure for a period of 6 weeks. The chronic renal failure results from removal of the right kidney and ligation of the segmental arteries which supply the upper and lower renal pole of the left kidney. The figure shows a small preglomerular artery with characteristic onion ring-like vessel wall proliferation and wall necrosis associated with severe hypertensive damage, called malignant nephrosclerosis (compare right of picture). A normal (as yet) undamaged arteriole is to be seen on the left.

FIG. 12 shows the histological changes in a Sprague-Dawley rat with chronic renal failure after Aranesp (EPO) treatment (0.1 µg/kg Aranesp) once a week starting immediately after induction of the chronic renal failure for a period of 6 weeks. The chronic renal failure results from removal of the right kidney and ligation of the segmental arteries which supply the upper and lower renal pole of the left kidney. The figure shows a normal glomerulus with delicate afferent vessel. There is no pathological tubulointerstitial finding.

FIG. 13 shows the histological changes in a Sprague-Dawley rat with chronic renal failure after Aranesp (EPO) treatment (0.1 µg/kg Aranesp) once a week starting immediately after induction of the chronic renal failure for a period of 6 weeks. The chronic renal failure results from removal of the right kidney and ligation of the segmental arteries which supply the upper and lower renal pole of the left kidney. The figure shows a normal glomerulus with delicate afferent vessel (630× magnification). There is no pathological tubulointerstitial finding.

FIG. 14 shows the histological changes in a Sprague-Dawley rat with chronic renal failure after Aranesp (EPO) treatment (0.1 µg/kg Aranesp) once a week starting immediately after induction of the chronic renal failure for a period of 6 weeks. The chronic renal failure results from removal of the right kidney and ligation of the segmental arteries which supply the upper and lower renal pole of the left kidney. The figure shows a normal glomerulus with delicate afferent vessel. There is no pathological tubulointerstitial finding.

FIG. 15 shows the histological changes in a Sprague-Dawley rat with chronic renal failure after Aranesp (EPO) treatment (0.1 µg/kg Aranesp) once a week starting immediately after induction of the chronic renal failure for a period of 6 weeks. The chronic renal failure results from removal of the right kidney and ligation of the segmental arteries which supply the upper and lower renal pole of the left kidney. The figure shows a normal glomerulus with delicate afferent vessel (630× magnification). There is no pathological tubulointerstitial finding.

EXAMPLE 1

Effect of EPO in Patients with Renal Anemia

The effect of erythropoietin in patients with renal anemia (Hb<10.5 g/dl) as a consequence of kidney disease in the terminal stage (preterminal renal failure; creatinine clearance <35 ml/min) was investigated. 11 patients were treated intravenously or subcutaneously with erythropoietin in weekly doses averaging 5 000 IU of rhEPO (recombinant human erythropoietin) for a period of at least 8 weeks. After erythropoietin treatment, the endothelial progenitor cells in the blood of the patients were investigated over a period of 20 weeks, analyzing endothelial progenitor cells for their number and their differentiation status by flow cytometry and a culture assay after 0, 2, 4, 6 and 8 weeks.

Circulating peripheral blood stem cells (CPBSC) comprise a small population of cells which express both the CD34 antigen and the CD45 antigen. An assay has been developed to determine the number of CPBSC by flow cytometry on the basis of the ISHAGE guidelines (Sutherland et al., J. Hematother., 5 (1996), 213-226). This assay was used to determine both the expression pattern of CD34 and CD45 cells and the morphology of the stem cells. Both the absolute number of CPBSC per µl and the proportion of CPBSC as a percentage of the total number of leukocytes was determined in this way.

Cell Culture Assay

Figure 1:
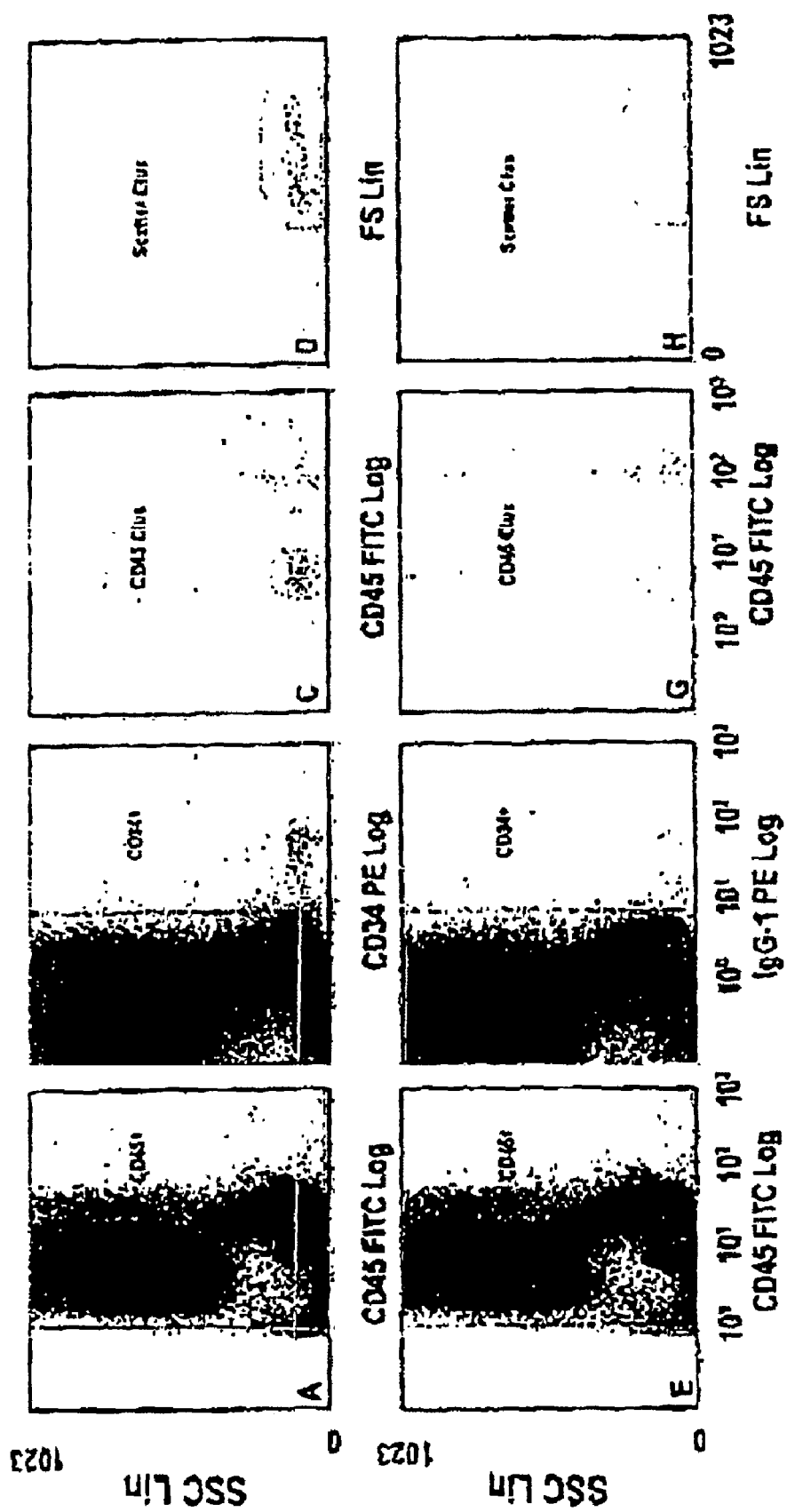
FIG. 1 shows the results of an FACS analysis of circulating CD34$^{30}$ stem cells based on the ISHAGE guidelines.
Figure 2:
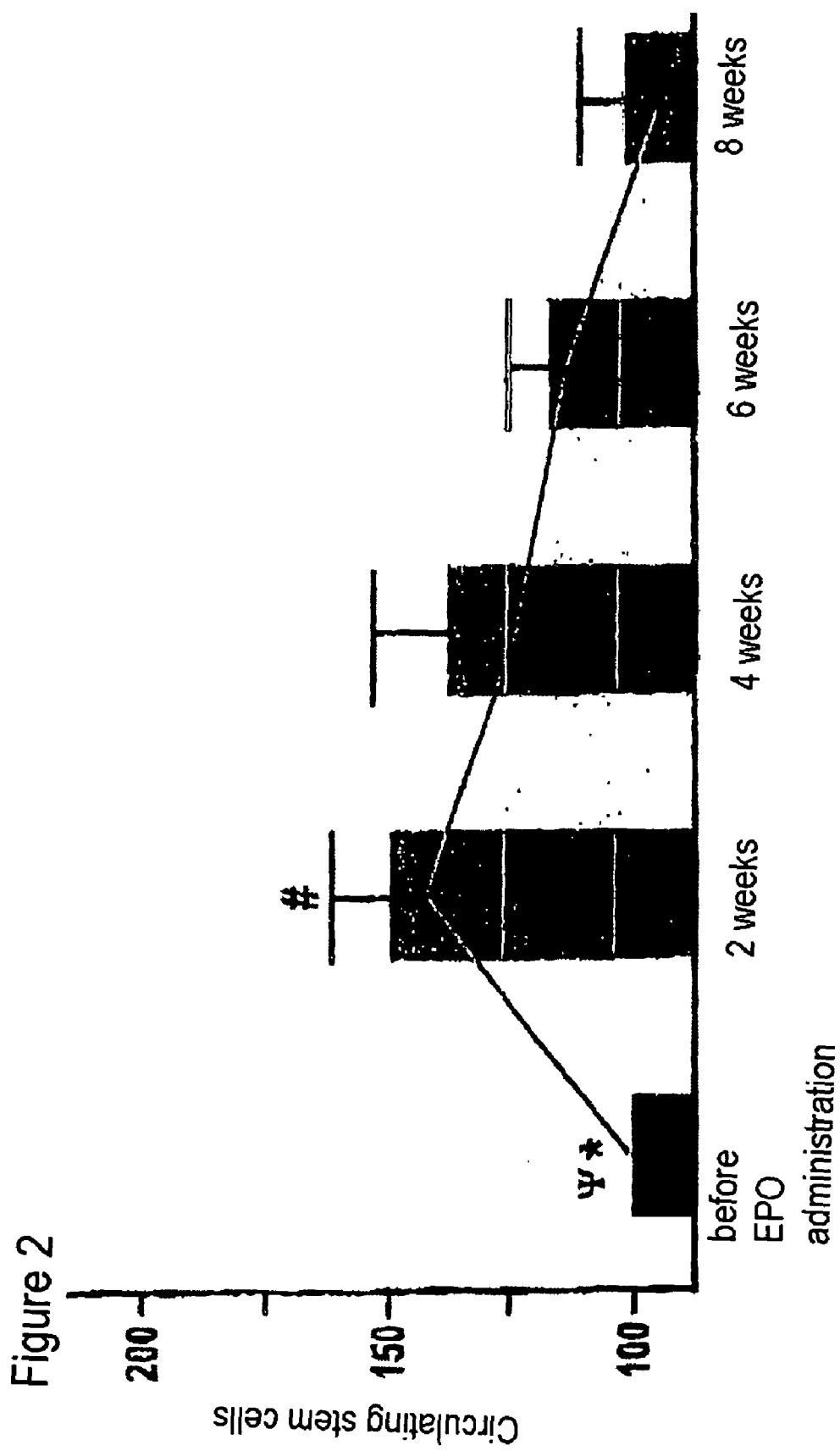
FIG. 2 shows the number of CD34$^{30}$ stem cells measured by FACS analysis over a period of 8 weeks.
Figure 3:
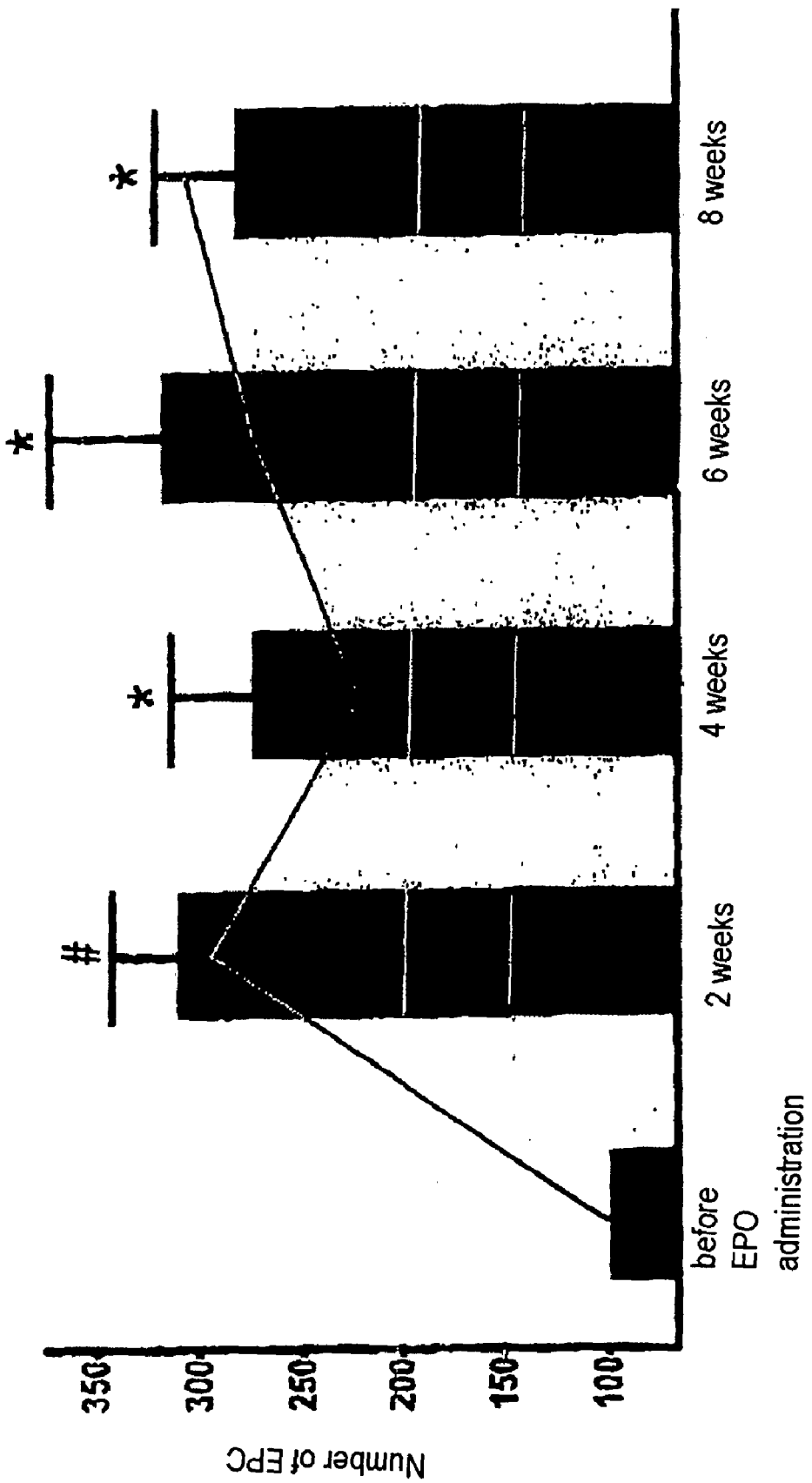

Peripheral blood mononuclear cells (PBMCs) were isolated by Ficoll density centrifugation from human blood samples in accordance with the method described in Asahara, Science, 275 (1997), 964-967. The cells were plated out on culture plates with fibronectin and maintained in EC basal medium. EC basal medium consists of EBM-2 basal medium (from Clonetics) and EGM-2 Quots (hEGF; GA-100 (gentamicin, amphotericin-B) FBS, VEGF, hFGF-B (w/heparin), R$^3$-IGF-1, ascorbic acid, heparin). After cultivation for 4 days, nonadherent cells were removed by washing the plates. The remaining adherent cells were treated with trypsin and plated out anew. They were then cultivated for a further 3 days. Cells with the endothelial phenotype were identified by positive staining for two different endothelial markers on day 7 after isolation. These are DiI-labeled acetylated low density lipoprotein (acLDL-DiI) and Ulex europaeus aglutinin-1 (UEA-1). The results of this investigation are depicted in FIG. 3.

Figure 4:
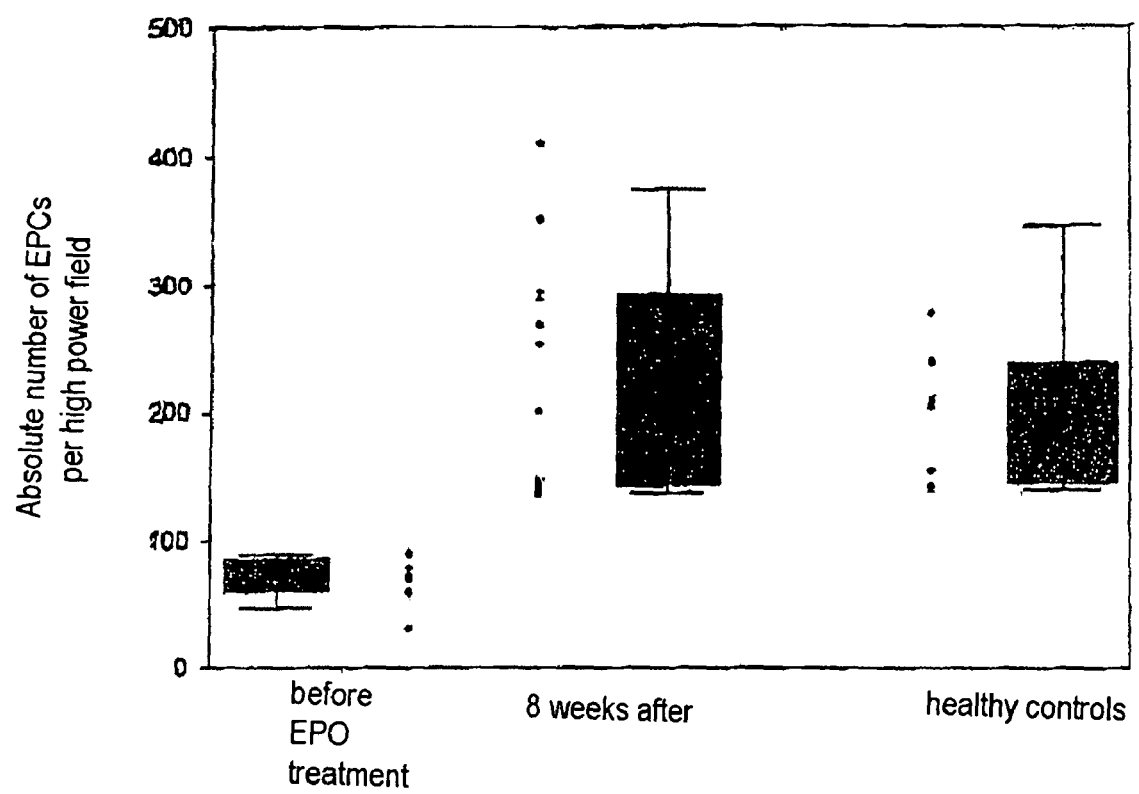

The results show that erythropoietin is able to mobilize endothelial progenitor cells and increase the number of circulating endothelial progenitor cells. Moreover, functional deficits which occur in certain pathological states such as renal anemia are compensated. These results are depicted in FIG. 4.

It was found by flow cytometry that the number of circulating $CD34^{30}$ stem cells in patients with renal disease in the terminal stage corresponds to the number of circulating $CD34^{30}$ stem cells in the blood of healthy subjects. After the erythropoietin treatment is started, the number of $CD34^{30}$ stem cells in the bloodstream increases significantly by more than 50%. It was determined by using the cell culture assay that there is a drastic increase in the number of cells developing an endothelial phenotype after treatment with erythropoietin. In a functional cell culture assay there was an increase of more than 3-fold in the greatly impaired ability of endothelial progenitor cells.

EXAMPLE 2

Improved Wound Healing Through Systemic Use of rhEPO

Figure 5:
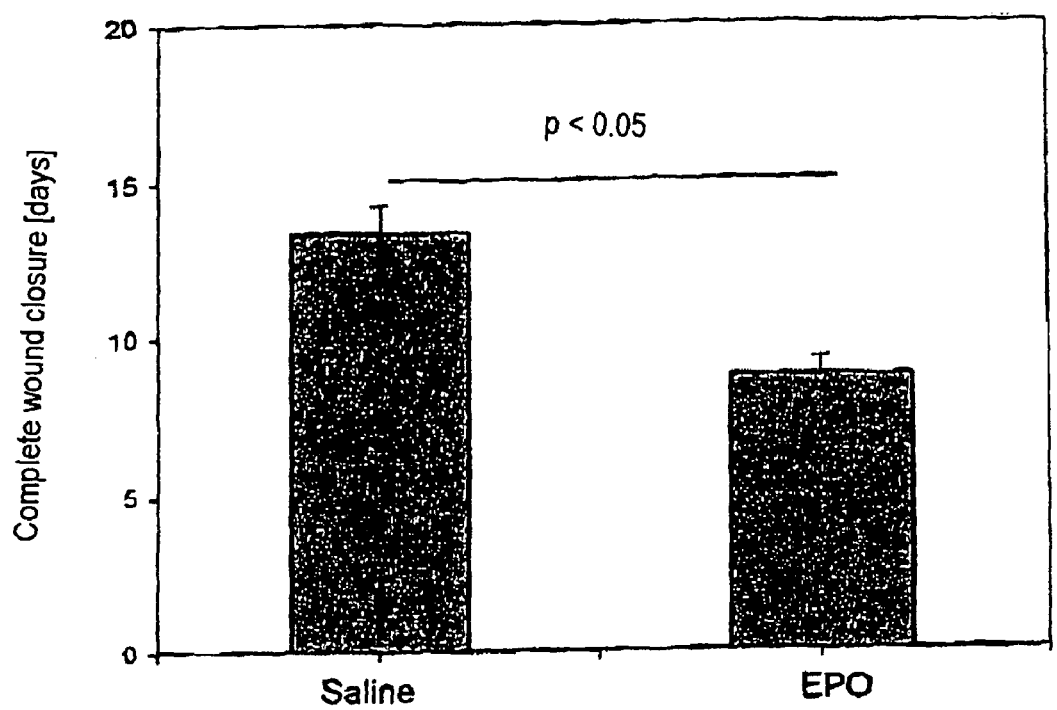

FVB/N mice were anesthetized by inhalation anesthesia with isoflorane. The fur on the two rear limbs was removed using a depilatory lotion and disinfected with 70% alcohol. A sterile 4 mm disposable biopsy tissue punch was used to make a skin wound on the right flank of each of the mice. The opposite side served as internal control. Postoperative antibiotic cover with penicillin G (20 000 units/kg) was performed once. Throughout the period of investigation, subcutaneous injections of the recombinant human erythropoietin analog Aranesp (0.1 μg/kg of body weight) took place once a week throughout the study period. The treatment started 7 days before removal of the tissue punch. The results are depicted in FIG. 5. They show that administration of EPO considerably expedites the wound healing process.

EXAMPLE 3

Reduction in the Progression of Chronic Renal Failure Through Erythropoietin Treatment 8-week-old Sprague-Dawley rats were anesthetized with ketamine (120 mg/kg) and Rompun (10 mg/kg). The right kidney was removed from the rats on day 0 and was fixed in formalin immediately after removal for histological examination. The segmental arteries which supply the upper and lower renal pole of the left kidney were ligated. This results in a renal infarction of the corresponding areas of the kidney, with only the middle third of the kidney remaining functional. The rats received subcutaneous (s.c.) injection of the erythropoietin analog Aranesp in a dose of 0.1 μg/kg of body weight or NaCl as control once a week.

Figure 7:
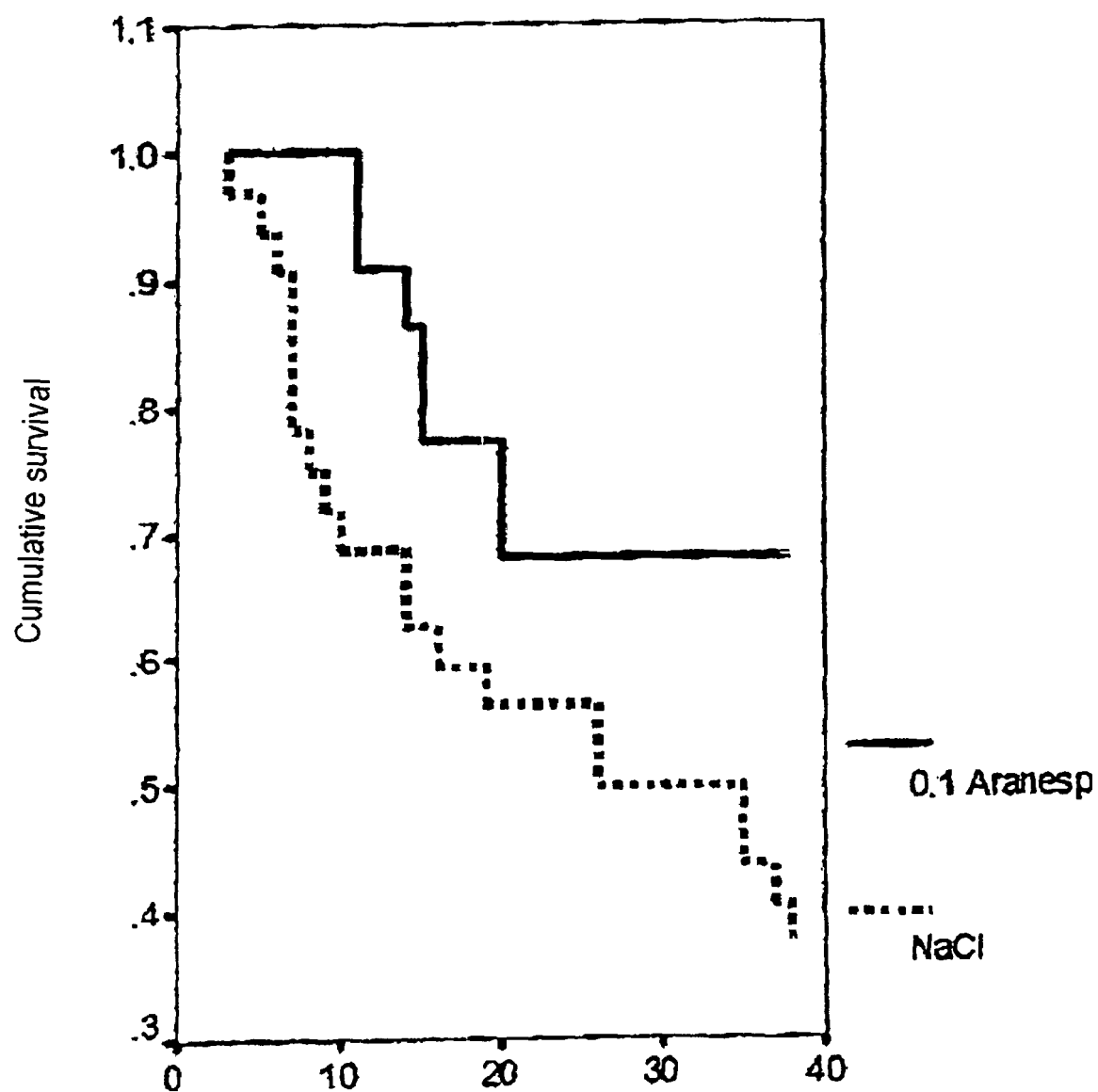
Figure 8:
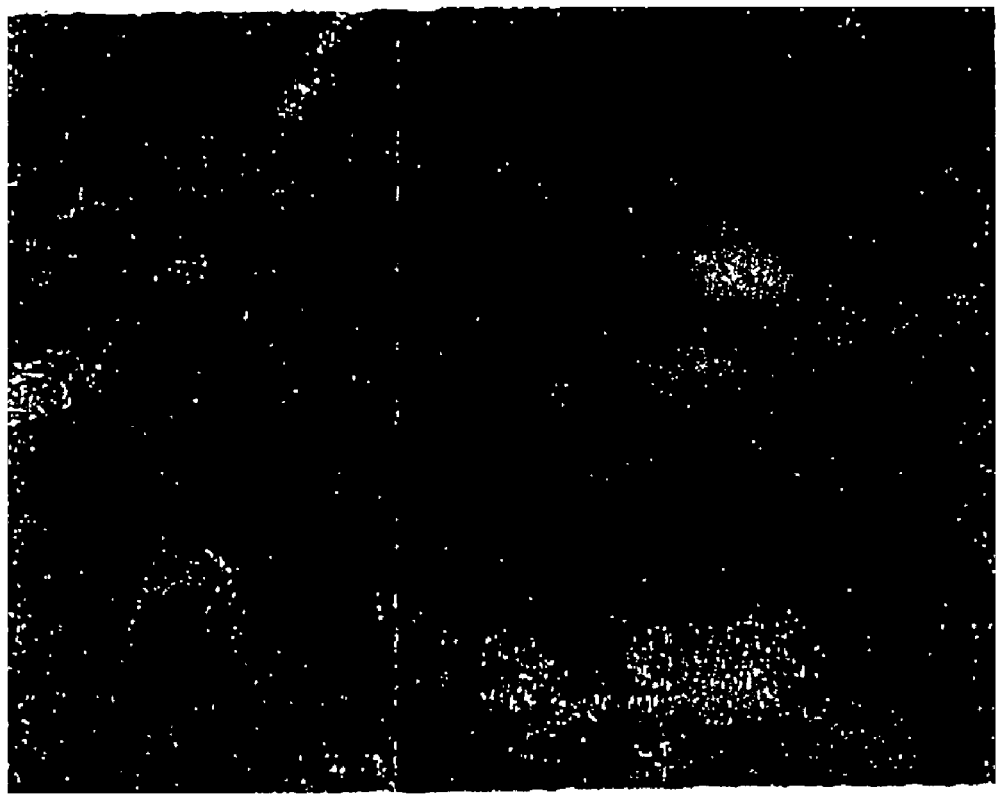
Figure 9:
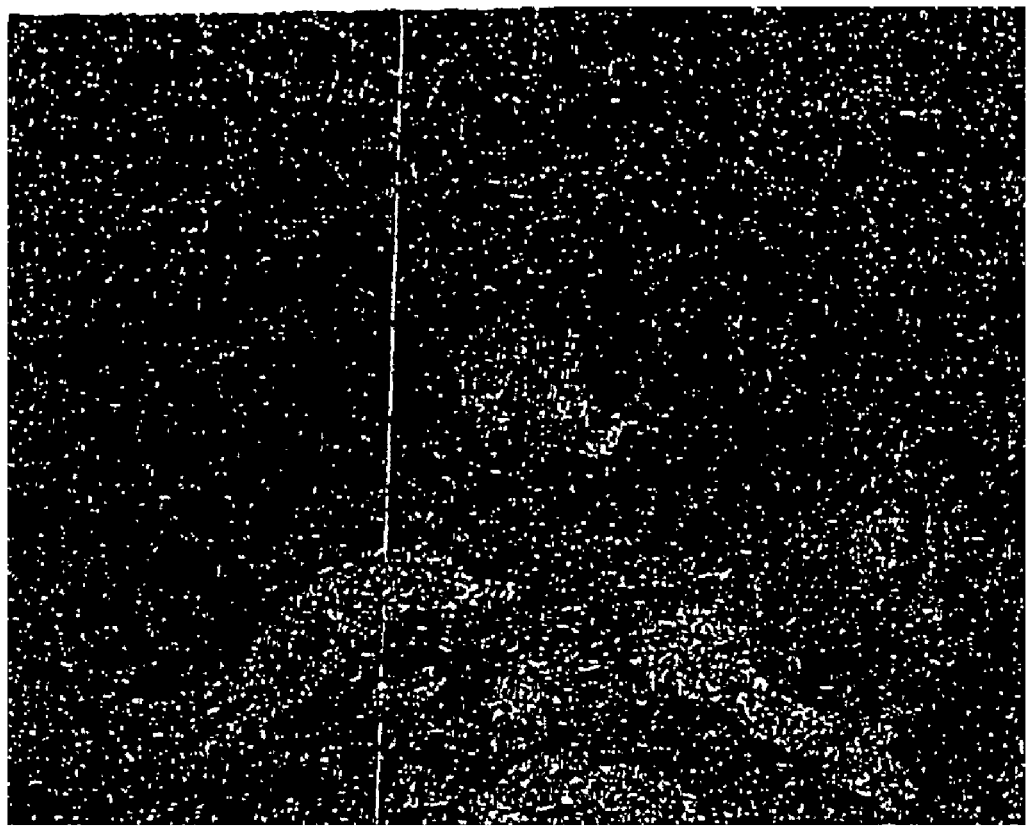
Figure 10:
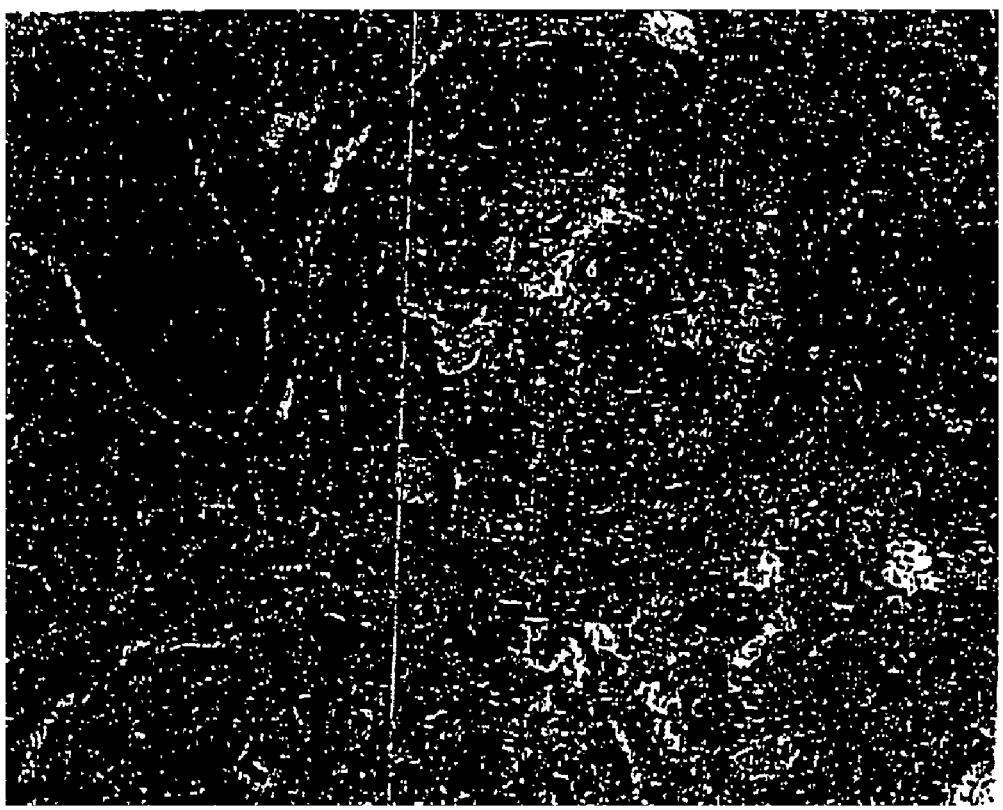
Figure 11:
Figure 12:
Figure 13:
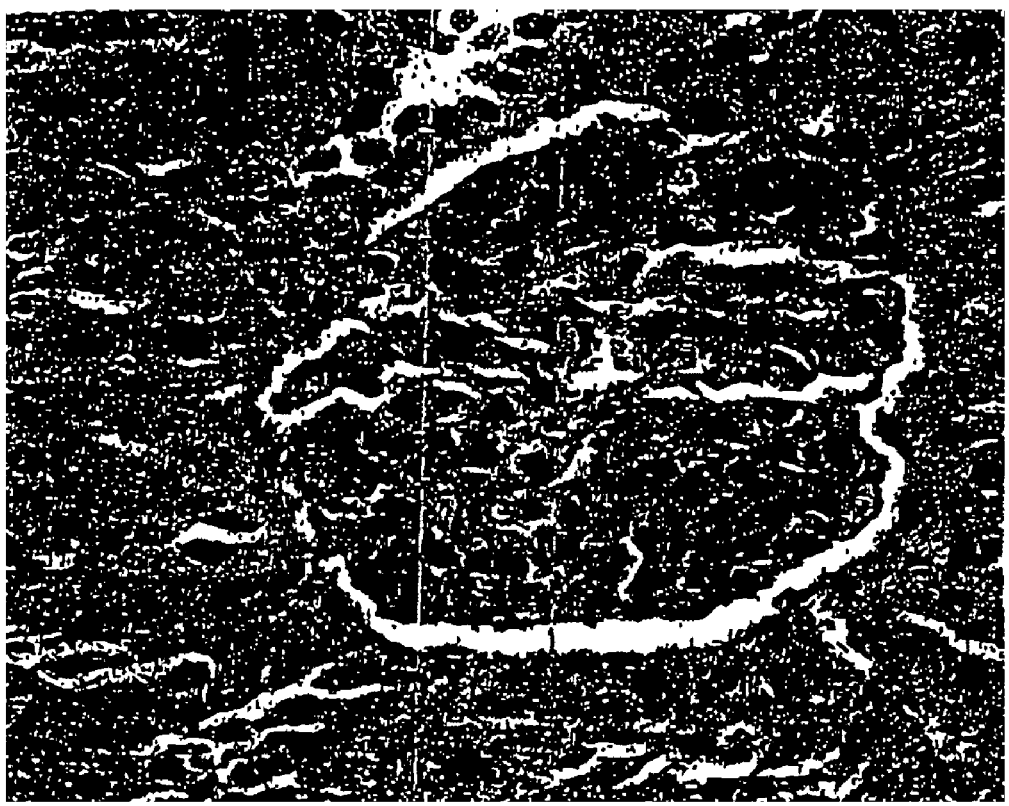
Figure 14:
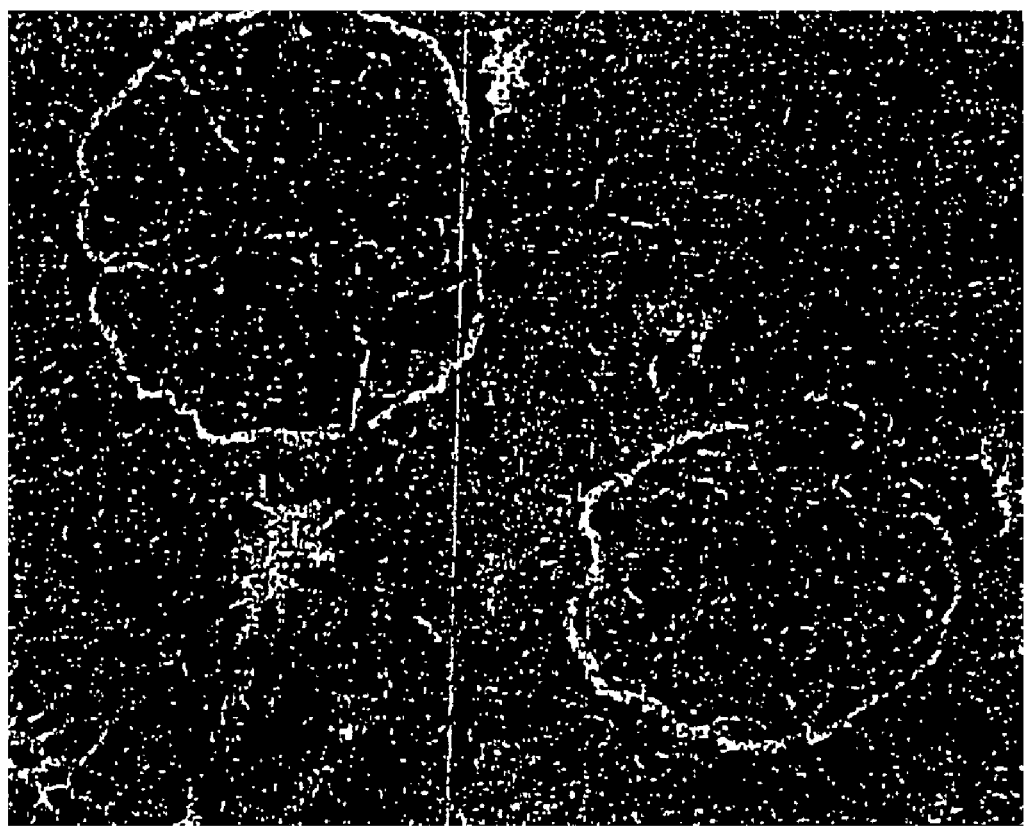
Figure 15:

FIG. 7 shows the Kaplan-Mayer survival plots for both experimental groups. The Aranesp-treated animals have distinctly improved survival compared with the control animals treated with sodium chloride.

FIGS. 12-15 show that the renal tissue shows no pathological changes after treatment with erythropoietin, whereas severe pathological changes are visible after treatment with NaCl (compare FIGS. 8-11). Further histological investigations revealed that a distinctly greater vessel density (CD31) is to be observed in Aranesp-treated animals than in animals treated with sodium chloride (data not shown).

EXAMPLE 4

Reduction in the Progression of Acute Renal Failure

Sprague-Dawley rats with a body weight of from 250 to 300 g were employed for this investigation. One of the experimental groups received Aranesp in a dose of 0.1 μg/kg of body weight once on the day before induction of the acute kidney failure. The rats were anesthetized with ketamine (120 mg/kg of body weight) and Rompun (10 mg/kg). A group of experimental animals which received s.c. injection of sodium chloride at the same time served as comparison. The blood flow in the kidney was stopped for 45 minutes by placing an arterial clamp on the right renal artery. A left nephrectomy was performed in this time. A sham operation was performed on a further control group. In this case, the abdomen was opened, the left renal artery was exposed but the blood supply was not stopped, and the contralateral right kidney was removed. All the animals were anesthetized for a period of 60 minutes and sacrificed 24 hours after the operation.

Figure 6:
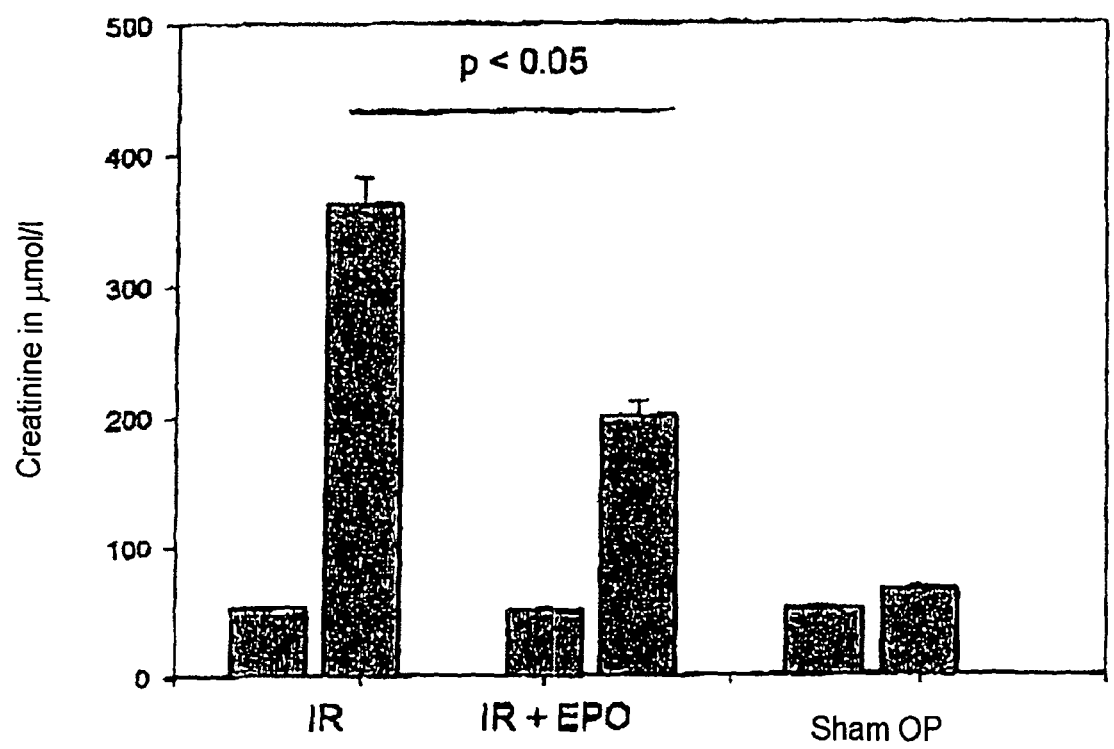

The 45-minute ischemia with subsequent reperfusion of the remaining right kidney led to extensive acute loss of renal function in the animals treated with sodium chloride. This was manifested by an increase by a factor of 7 in the serum creatinine level ($p<0.05$). By contrast, the animals treated with the erythropoietin analog Aranesp showed only a four-fold increase in the serum creatinine level one day after induction of the ischemia-reperfusion damage. There was no increase in the retention values in the animals which underwent left nephrectomy and a sham operation on the right kidney. The results are depicted in FIG. 6.

The invention claimed is:

1. A method for diabetic wound healing, said method comprising administering a pharmaceutical composition comprising a subpolycythemic erythropoietin weekly dose of 1 to 90 international units (IU) EPO/kg body weight to a subject in need of said wound healing for healing of said diabetic wound.

2. The method of claim 1, wherein the pharmaceutical composition is administered parenterally.

3. The method of claim 2, wherein said parenteral administration is carried out using a mode selected from the group consisting of intravenous, intramuscular, intracutaneous and subcutaneous, administration.

4. The method of claim 1, where the pharmaceutical composition is administered via pulmonary administration.

5. The method of claim 1, wherein the pharmaceutical composition is orally administered.

6. The method of claim 1, where the pharmaceutical composition comprises at least one further active ingredient which stimulates endothelial progenitor cells.

7. The method of claim 1, wherein the erythropoietin is human or animal erythropoietin.

* * * * *